(12) United States Patent
Aissaoui et al.

(10) Patent No.: US 8,133,901 B2
(45) Date of Patent: Mar. 13, 2012

(54) 3-HETEROARYL (AMINO OR AMIDO)-1-(BIPHENYL OR PHENYLTHIAZOLYL) CARBONYLPIPERIDINE DERIVATIVES AS OREXIN RECEPTOR INHIBITORS

(75) Inventors: Hamed Aissaoui, Pulversheim (FR); Christoph Boss, Allschwil (CH); Markus Gude, Allschwil (CH); Ralf Koberstein, Lorrach (DE); Thierry Sifferlen, Wentzwiller (FR)

(73) Assignee: Actelion Pharmaceuticals Ltd., Allschwil (CH)

( * ) Notice: Subject to any disclaimer, the term of this patent is extended or adjusted under 35 U.S.C. 154(b) by 324 days.

(21) Appl. No.: 12/517,010

(22) PCT Filed: Nov. 29, 2007

(86) PCT No.: PCT/IB2007/054851
§ 371 (c)(1),
(2), (4) Date: May 29, 2009

(87) PCT Pub. No.: WO2008/065626
PCT Pub. Date: Jun. 5, 2008

(65) Prior Publication Data
US 2010/0069418 A1    Mar. 18, 2010

(30) Foreign Application Priority Data
Dec. 1, 2006   (WO) .................. PCTIB2006/054549

(51) Int. Cl.
C07D 401/12      (2006.01)
C07D 417/14      (2006.01)
C07D 513/04      (2006.01)
A61K 31/506      (2006.01)

(52) U.S. Cl. .................. 514/275; 514/320; 546/269.7; 546/270.1; 544/330; 544/331; 544/332

(58) Field of Classification Search .................. 544/330, 544/331, 332; 546/269.7, 270.1; 514/275, 514/320
See application file for complete search history.

(56) References Cited

U.S. PATENT DOCUMENTS

| | | | |
|---|---|---|---|
| 3,282,927 A | 11/1966 | Thomas et al. |
| 4,267,339 A | 5/1981 | Tedeschi et al. |
| 6,191,124 B1 | 2/2001 | Smith et al. |
| 7,994,336 B2 | 8/2011 | Aissaoui et al. |
| 2003/0186964 A1 | 10/2003 | Branch et al. |
| 2004/0058921 A1 | 3/2004 | Branch et al. |
| 2004/0143115 A1 | 7/2004 | Branch et al. |
| 2004/0180887 A1 | 9/2004 | Branch et al. |
| 2004/0192673 A1 | 9/2004 | Gaillard et al. |
| 2004/0215014 A1 | 10/2004 | Chan et al. |
| 2004/0242575 A1 | 12/2004 | Branch et al. |
| 2006/0014733 A1 | 1/2006 | Howard et al. |
| 2006/0040937 A1 | 2/2006 | Branch et al. |
| 2006/0252769 A1 | 11/2006 | Branch et al. |
| 2010/0016401 A1 | 1/2010 | Aissaoui et al. |
| 2010/0113531 A1 | 5/2010 | Aissaoui et al. |
| 2010/0152191 A1 | 6/2010 | Coleman et al. |
| 2010/0168134 A1 | 7/2010 | Breslin et al. |
| 2010/0184808 A1 | 7/2010 | Aissaoui et al. |
| 2010/0197733 A1 | 8/2010 | Aissaoui et al. |
| 2010/0204285 A1 | 8/2010 | Aissaoui et al. |
| 2010/0222328 A1 | 9/2010 | Aissaoui et al. |
| 2011/0009401 A1 | 1/2011 | Aissaoui et al. |
| 2011/0009461 A1 | 1/2011 | Aissaoui et al. |
| 2011/0039857 A1 | 2/2011 | Aissaoui et al. |
| 2011/0124636 A1 | 5/2011 | Aissaoui et al. |

FOREIGN PATENT DOCUMENTS

| | | |
|---|---|---|
| EP | 1484327 | 1/2007 |
| GB | 1493048 | 11/1977 |
| WO | WO 95/29922 | 11/1995 |
| WO | WO 02/46158 | 6/2002 |
| WO | WO 03/051368 | 6/2003 |

(Continued)

OTHER PUBLICATIONS

Damasio, Alzheimer's Disease and Related Dementias, Cecil Textbook of Medicine, 20th Edition, vol. 2, pp. 1992-1996, 1996.*

(Continued)

*Primary Examiner* — Deepak Rao
(74) *Attorney, Agent, or Firm* — Hoxie & Associates LLC; Brittany La

(57) ABSTRACT

The invention relates to piperidine compounds of formula (I):

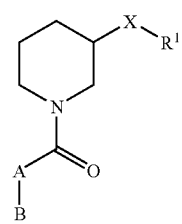

(I)

wherein X—$R^1$ represents —N(H)-pyrimidinyl, wherein said pyrimidinyl is unsubstituted or mono-substituted wherein the substituent is selected from ($C_{1-4}$)alkyl or halogen, or X—$R^1$ represents —NH—C(O)-heterocyclyl, wherein the heterocyclyl is selected from benzofuranyl and imidazo[2,1-b]-thiazolyl, wherein said heterocyclyl is unsubstituted or independently mono-, di- or tri-substituted wherein the substituents are independently selected from ($C_{1-4}$)alkyl; A represents a phenyl- or thiazolyl-group, wherein the phenyl or thiazolyl is unsubstituted or mono-substituted with ($C_{1-4}$)alkyl; B represents a phenyl-group, wherein the phenyl is unsubstituted or mono-, or di- substituted, wherein the substituents are independently selected from the group consisting of ($C_{1-4}$)alkyl, ($C_{1-4}$)alkoxy, trifluoromethyl, cyano and halogen; to pharmaceutically acceptable salts thereof, and to the use of such compounds use as medicaments, especially as orexin receptor antagonists.

10 Claims, No Drawings

FOREIGN PATENT DOCUMENTS

| WO | WO 03/051873 | 6/2003 |
|----|--------------|--------|
| WO | WO 2004/041791 | 5/2004 |
| WO | WO 2004/041807 | 5/2004 |
| WO | WO 2004/041816 | 5/2004 |
| WO | WO 2006/011042 | 2/2006 |

OTHER PUBLICATIONS

Layzer, Degenerative Diseases of the Nervous System, Cecil Textbook of Medicine, 20th Edition, vol. 2, pp. 2050-2057, 1996.*

Fadel et al., Orexin/hypocretin modulation of the basal forebrain cholinergic system: Insights from in vivo microdialysis studies, Pharmacology, Biochemistry and Behavior 90 (2008), pp. 156-162.*

Yamanaka et al., New Approaches for the Study of Orexin Function, Journal of Neuroendocrinology, 22, pp. 818-824 (2010).*

Chemelli, R.M. et al., "Narcolepsy in orexin Knockout Mice: Molecular Genetics of Sleep Regulation." Cell, 1999, vol. 98, 437-451.

Eicher, T. et al., "The Chemistry of Heterocycles: Structure, Reactions, Syntheses and Applications", 2nd edition 2003, Wiley-Vch, ISBN 978-3-527-30720-3.

Gould, P. et al., "Salt Selection for Basic Drugs", Int. J. Pharm. (1988), vol. 33, 201-217.

Hamamoto, H. et al., "Chemoenzymatic synthesis of the C-13 side chain of paclitaxel (Taxol) and docetaxel (Taxotere)," Tetrahedron Asymmetry 2000, 11, 4485-4497.

Sakurai, T. et. al., "Orexins and Orexin Receptors: A Family of Hypothalamic Neuropeptides and G Protein-Coupled Receptors that Regulate Feeding Behavior." Cell, 1998, vol. 92, 573-585.

Aissaoui, H., et al., "N-Glycine-Sulfonamides as Potent Dual Orexin 1/Orexin 2 Receptor Antagonists", Bioorganic & Medicinal Chemistry Letters, vol. 18, pp. 5729-5733, (2008).

Böhm, H., et al., "Scaffold Hopping", Drug Discovery Today: Technologies, vol. 1, No. 3, pp. 217-224, (2004).

Boss, C., et al., "Biomedical Application of Orexin/Hypocretin Receptor Ligands in Neuroscience", Journal of Medicinal Chemistry, vol. 52, No. 4, pp. 891-903, (2009).

Boss, C., et al., "Orexin Receptor Antagonism: A New Principle in Neuroscience", CHIMIA, vol. 62, No. 12, pp. 974-979, (2008).

Cai, J., et al., "Antagonists of the Orexin Receptors", Expert Opinion on Therapeutic Patents, vol. 16, No. 5, pp. 631-646, (2006).

Gatfield, J., et al., "Orexin Receptor Antagonists: A New Concept in CNS Disorders", ChemMedChem, vol. 5, pp. 1197-1214, (2010).

Langmead, C., et al., "Characterisation of the Binding of [$^3$H]-SB-674042, a Novel Nonpeptide Antagonist, to the Human Orexin-1 Receptor", British Journal of Pharmacology, vol. 141, pp. 340-346, (2004).

Sifferlen, T., et al., "Novel Pyrazolo-Tetrahydropyridines as Potent Orexin Receptor Antagonists", Bioorganic & Medicinal Chemistry Letters, vol. 20, pp. 1539-1542, (2010).

Office Action of U.S. Appl. No. 12/311,451 dated Aug. 11, 2011 for U.S. Appl. No. 12/311,451.

* cited by examiner

3-HETEROARYL (AMINO OR AMIDO)-1-(BIPHENYL OR PHENYLTHIAZOLYL) CARBONYLPIPERIDINE DERIVATIVES AS OREXIN RECEPTOR INHIBITORS

CROSS REFERENCE TO RELATED APPLICATIONS

This application is a U.S. filing under 35 USC 371 of PCT/IB2007/054851 filed on Nov. 29, 2007, which claims the benefit of PCT/IB2006/054549 filed on Dec. 1, 2006, the contents of each of which are incorporated herein by reference.

The present invention relates to novel piperidine compounds of formula (I) and their use as pharmaceuticals. The invention also concerns related aspects including processes for the preparation of the compounds, pharmaceutical compositions containing one or more compounds of formula (I), and especially their use as orexin receptor antagonists.

Orexins (orexin A or OX-A and orexin B or OX-B) are novel neuropeptides found in 1998 by two research groups, orexin A is a 33 amino acid peptide and orexin B is a 28 amino acid peptide (Sakurai T. et al., Cell, 1998, 92, 573-585). Orexins are produced in discrete neurons of the lateral hypothalamus and bind to the G-protein-coupled receptors ($OX_1$ and $OX_2$ receptors). The orexin-1 receptor ($OX_1$) is selective for OX-A, and the orexin-2 receptor ($OX_2$) is capable to bind OX-A as well as OX-B. Orexins are found to stimulate food consumption in rats suggesting a physiological role for these peptides as mediators in the central feedback mechanism that regulates feeding behaviour (Sakurai T. et al., Cell, 1998, 92, 573-585). On the other hand, it was also observed that orexins regulate states of sleep and wakefulness opening potentially novel therapeutic approaches to narcolepsy as well as insomnia and other sleep disorders (Chemelli R. M. et al., Cell, 1999, 98, 437-451).

Orexin receptors are found in the mammalian brain and may have numerous implications in pathologies such as dysthymic, mood, psychotic and anxiety disorders; diabetes and appetite, taste, eating, or drinking disorders; hypothalamic diseases; disturbed biological and circadian rhythms; sleep disturbances associated with diseases such as neurological disorders, neuropathic pain and restless leg syndrome; insomnias related to psychiatric disorders; sleep apnea; narcolepsy; idiopathic insomnias; parasomnias; benign prostatic hypertrophy; all dementias and cognitive dysfunctions in the healthy population and in psychiatric and neurologic disorders; and other diseases related to general orexin system dysfunctions.

The present invention provides piperidine derivatives, which are non-peptide antagonists of human orexin receptors. These compounds are in particular of potential use in the treatment of e.g. eating disorders, drinking disorders, sleep disorders, or cognitive dysfunctions in psychiatric and neurologic disorders.

Up to now, several low molecular weight compounds are known having a potential to antagonise either specifically $OX_1$ or $OX_2$, or both receptors at the same time. Piperidine derivatives useful as orexin receptor antagonists are disclosed in WO01/096302.

Nitrogenous heterocyclic compounds useful for a disease for which sodium channel inhibition is effective are described in EP 1484327. 1,3-Substituted cycloamino derivatives useful as histamine-3 receptor antagonists are described in WO 2006/011042.

i) The present invention consists of compounds of the formula (I)

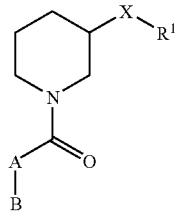

(I)

wherein
$X$—$R^1$ represents —N(H)-pyrimidinyl, wherein said pyrimidinyl is unsubstituted or mono-substituted wherein the substituent is selected from ($C_{1-4}$)alkyl or halogen, or
$X$—$R^1$ represents —NH—C(O)-heterocyclyl, wherein the heterocyclyl is selected from benzofuranyl and imidazo[2,1-b]-thiazolyl, wherein said heterocyclyl is unsubstituted or independently mono-, di-, or tri-substituted wherein the substituents are independently selected from ($C_{1-4}$)alkyl;
A represents a phenyl- or thiazolyl-group, wherein the phenyl or thiazolyl is unsubstituted or mono-substituted with ($C_{1-4}$)alkyl;
B represents a phenyl-group, wherein the phenyl is unsubstituted or mono-, or di-substituted, wherein the substituents are independently selected from the group consisting of ($C_{1-4}$)alkyl, ($C_{1-4}$)alkoxy, trifluoromethyl, cyano and halogen.

In this patent application, an arrow shows the point of attachment of the radical drawn. For example, the radical drawn below

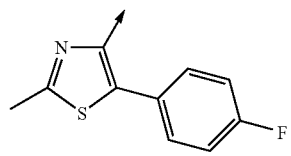

is the 5-(4-fluoro-phenyl)-2-methyl-thiazol-4-yl group.

The compounds of formula (I) may contain one or more stereogenic or asymmetric centers, such as one or more asymmetric carbon atoms. The compounds of Formula (I) may thus be present as mixtures of stereoisomers or preferably as pure stereoisomers. Mixtures of stereoisomers may be separated in a manner known to a person skilled in the art.

The term "halogen" means fluorine, chlorine, or bromine, preferably fluorine or chlorine.

The term "($C_{1-4}$)alkyl", alone or in combination, means a straight-chain or branched-chain alkyl group with 1 to 4 carbon atoms. Examples of ($C_{1-4}$)alkyl groups are methyl, ethyl, propyl, isopropyl, n-butyl, isobutyl, sec.-butyl or tert.-butyl. Preferred are methyl and ethyl.

The term "($C_{1-4}$)alkoxy", alone or in combination, means a group of the formula ($C_{1-4}$)alkyl-O— in which the term "($C_{1-4}$)alkyl" has the previously given significance, such as methoxy, ethoxy, n-propoxy, isopropoxy, n-butoxy, isobutoxy, sec.-butoxy or tert.-butoxy. Preferred are methoxy and ethoxy.

The phenyl-group may be unsubstituted or mono-, or di-substituted, wherein the substituents are independently selected from the group consisting of (C$_{1-4}$)alkyl, (C$_{1-4}$)alkoxy, trifluoromethyl, cyano and halogen.

In case "A" represents "phenyl" the term preferably means a phenyl-group, wherein the phenyl is unsubstituted or mono-substituted with (C$_{1-4}$)alkyl. Especially, the phenyl-group is unsubstituted. In addition to the above-mentioned substituents, the group "A" is also substituted by the substituent "B", wherein B is preferably attached in ortho position to the point of attachment of the carbonyl group which links A to the rest of the molecule.

In case "B" represents "phenyl" the term preferably means a phenyl-group, wherein the phenyl is unsubstituted or mono-, or di-substituted, wherein the substituents are independently selected from the group consisting of (C$_{1-4}$)alkyl, (C$_{1-4}$)alkoxy, trifluoromethyl, cyano and halogen. More preferred the substituents are independently selected from the group consisting of (C$_{1-4}$)alkyl, (C$_{1-4}$)alkoxy, trifluoromethyl and halogen. In a further preferred embodiment, the substituents are independently selected from the group consisting of methyl, ethyl, methoxy, trifluoromethyl, fluorine and chlorine.

In case "A" and "B" both represents "phenyl" the combination "A-B" preferably means a biphenyl group which is unsubstituted for "A" and unsubstituted or mono-, di- or tri-substituted for "B", wherein the substituents are independently selected from the group consisting of (C$_{1-4}$)alkyl, (C$_{1-4}$)alkoxy, trifluoromethyl and halogen, especially from (C$_{1-4}$)alkyl, (C$_{1-4}$)alkoxy and halogen. Further preferred examples of substituents for "B" are methyl, methoxy and fluorine.

Examples of such biphenyl groups "A-B" are:

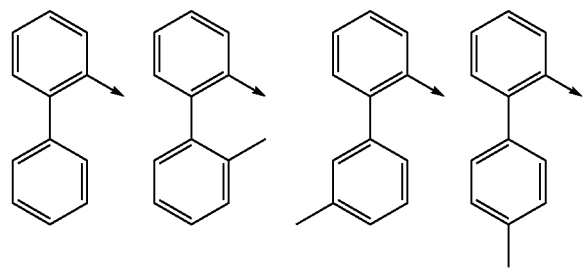

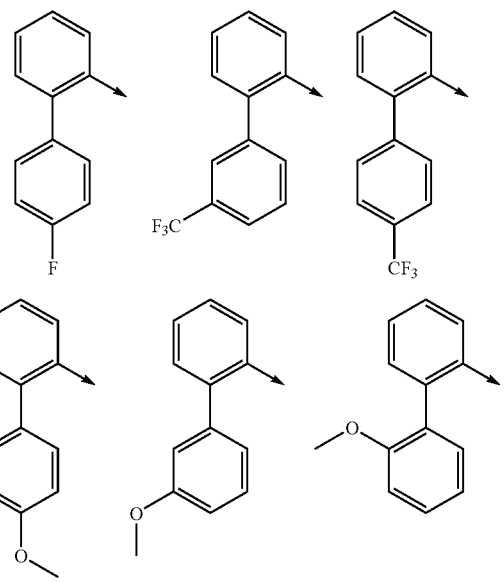

The thiazolyl-group as defined for group "A", may be unsubstituted or mono-substituted with (C$_{1-4}$)alkyl. Preferably, the thiazolyl-group is mono-substituted with methyl. In addition to the above-mentioned substituents, the group "A" is also substituted by the substituent "B", whereby B is preferably attached in ortho position to the point of attachment of the carbonyl group which links A to the rest of the molecule; most preferably the group A-CO— is a thiazole-4-carbonyl-5-yl group.

Examples wherein "A" represents a thiazolyl-group and B represents a phenyl-group are:

-continued

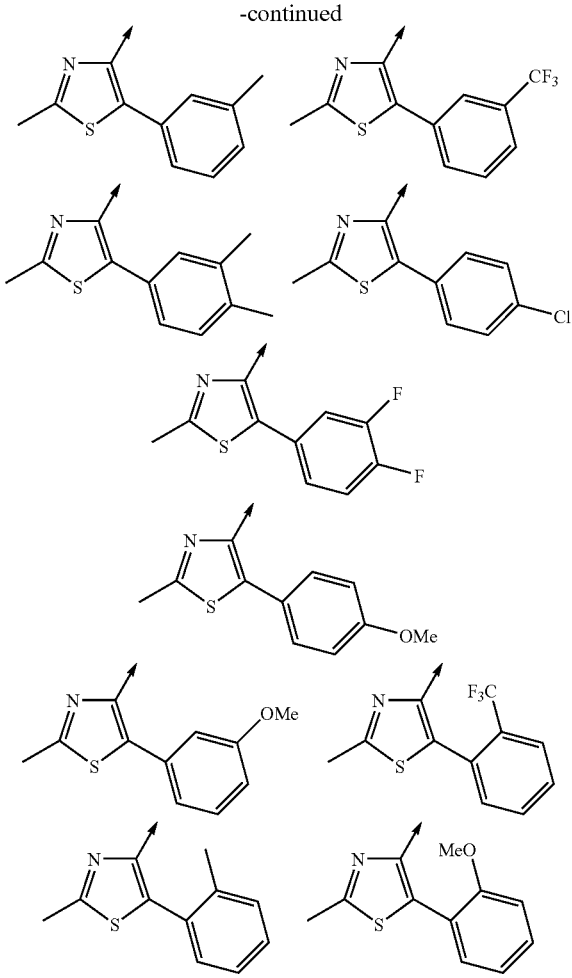

In case X represents the group "NH—C(O)", the carbonyl part of said group is preferably connected to R¹.

In an embodiment of the invention, in case X—R¹ represents —N(H)-pyrimidinyl, wherein said pyrimidinyl is unsubstituted or mono-substituted (preferably mono-substituted) wherein the substituents are independently selected from the group consisting of $(C_{1-4})$alkyl and halogen, the substituent is preferably halogen, especially bromine. An example of R¹ as used for the substituent "—NH—R¹" is:

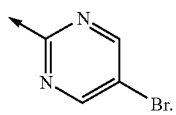

In another embodiment of the invention, in case X—R¹ represents —NH—C(O)—heterocyclyl, wherein the heterocyclyl is imidazo[2,1-b]-thiazolyl, said imidazo[2,1-b]-thiazolyl is unsubstituted or mono-, di-, or tri-substituted (especially mono-substituted) wherein the substituents are independently selected from $(C_{1-4})$alkyl (especially methyl).

In another embodiment of the invention, in case X—R¹ represents —NH—C(O)—heterocyclyl, wherein the heterocyclyl is benzofuranyl, said benzofuranyl is preferably unsubstituted.

Examples of R¹ as used for the substituent "—NH—C(O)—R¹" are:

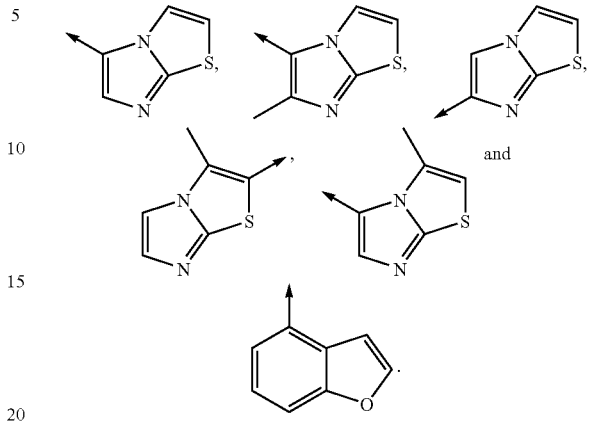

Especially, examples of R¹ as used for the substituent "—NH—C(O)—R¹" are:

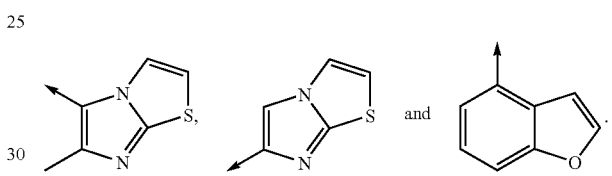

Preferred is 6-methyl-imidazo[2,1-b]thiazole-5-yl.

ii) A further embodiment of the invention relates to compounds of formula (I) according to embodiment i) which are also compounds of the formula (Ia), wherein the stereogenic center in position 3 of the piperidine ring is in absolute (R)-configuration

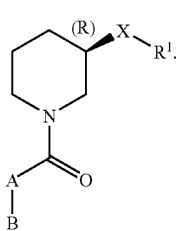

iii) A further embodiment of the invention comprises compounds of the formula (I) according to embodiments i) or ii), wherein A represents a phenyl- or thiazolyl-group, wherein the phenyl or thiazolyl is unsubstituted or mono-substituted with $(C_{1-4})$alkyl; and B represents a phenyl-group, wherein the phenyl is mono-, or di-substituted, wherein the substituents are independently selected from the group consisting of $(C_{1-4})$alkyl, $(C_{1-4})$alkoxy, trifluoromethyl, and halogen.

iv) A further embodiment of the invention comprises compounds of the formula (I) according to embodiments i) or ii), wherein A represents a phenyl-group, wherein the phenyl is unsubstituted or mono-substituted with $(C_{1-4})$alkyl; and B represents a phenyl-group, wherein the phenyl is mono-, or di-substituted, wherein the substituents are independently selected from the group consisting of $(C_{1-4})$alkyl, $(C_{1-4})$alkoxy, trifluoromethyl, and halogen.

v) A further embodiment of the invention comprises compounds of the formula (I) according to embodiments i) or ii), wherein A represents a thiazolyl-group, wherein the thiazolyl is unsubstituted or mono-substituted with $(C_{1-4})$alkyl;

B represents a phenyl-group, wherein the phenyl is mono-, or di-substituted, wherein the substituents are independently selected from the group consisting of methyl, ethyl, methoxy, trifluoromethyl, fluorine and chlorine.

vi) A further embodiment of the invention comprises compounds of the formula (I) according to any one of embodiments i) to v), wherein X—$R^1$ represents —N(H)-pyrimidinyl, wherein said pyrimidinyl is mono-substituted wherein the substituent is selected from $(C_{1-4})$alkyl or halogen, or X—$R^1$ represents —NH—C(O)imidazo[2,1-b]-thiazolyl, wherein said imidazo[2,1-b]-thiazolyl is mono-, di-, or tri-substituted wherein the substituents are independently selected from $(C_{1-4})$alkyl.

vii) A further embodiment of the invention comprises compounds of the formula (I) according to any one of embodiments i) to v), wherein $R^1$ represents imidazo[2,1-b]-thiazolyl, wherein said imidazo[2,1-b]-thiazolyl is unsubstituted or mono-, di-, or tri-substituted wherein the substituents are independently selected from $(C_{1-4})$alkyl.

viii) A further embodiment of the invention comprises compounds of the formula (I) according to any one of embodiments i) to yl), wherein X represents NH.

ix) A further embodiment of the invention comprises compounds of the formula (I) according to any one of embodiments i) to vii), wherein X represents NH—C(O).

x) Preferred compounds of formula (I) according to embodiment i) are selected from the group consisting of:

(R)-Biphenyl-2-yl-[3-(5-bromo-pyrimidin-2-ylamino)-piperidin-1-yl]-methanone;
(R)-[3-(5-Bromo-pyrimidin-2-ylamino)-piperidin-1-yl]-(4'-methoxy-biphenyl-2-yl)-methanone;
(R)-[3-(5-Bromo-pyrimidin-2-ylamino)-piperidin-1-yl]-(2'-fluoro-biphenyl-2-yl)-methanone;
(R)-[3-(5-Bromo-pyrimidin-2-ylamino)-piperidin-1-yl]-(3'-fluoro-biphenyl-2-yl)-methanone;
(R)-[3-(5-Bromo-pyrimidin-2-ylamino)-piperidin-1-yl]-(3',4'-dimethyl-biphenyl-2-yl)-methanone;
(R)-Benzofuran-4-carboxylic acid{1-[5-(4-fluoro-phenyl)-2-methyl-thiazole-4-carbonyl]-piperidin-3-yl}amide;
(R)-6-Methyl-imidazo[2,1-b]thiazole-5-carboxylic acid[1-(2-methyl-5-m-tolyl-thiazole-4-carbonyl)-piperidin-3-yl]-amide;
(R)-6-Methyl-imidazo[2,1-b]thiazole-5-carboxylic acid {1-[5-(4-fluoro-phenyl)-2-methyl-thiazole-4-carbonyl]-piperidin-3-yl}-amide;
(R)-6-Methyl-imidazo[2,1-b]thiazole-5-carboxylic acid[1-(2-methyl-5-p-tolyl-thiazole-4-carbonyl)-piperidin-3-yl]-amide;
(R)-6-Methyl-imidazo[2,1-b]thiazole-5-carboxylic acid {1-[5-(4-ethyl-phenyl)-2-methyl-thiazole-4-carbonyl]-piperidin-3-yl}-amide;
(R)-6-Methyl-imidazo[2,1-b]thiazole-5-carboxylic acid {1-[5-(3-fluoro-phenyl)-2-methyl-thiazole-4-carbonyl]-piperidin-3-yl}-amide;
(R)-6-Methyl-imidazo[2,1-b]thiazole-5-carboxylic acid {1-[2-methyl-5-(3-trifluoro-phenyl)-thiazole-4-carbonyl]-piperidin-3-yl}-amide;
(R)-6-Methyl-imidazo[2,1-b]thiazole-5-carboxylic acid {1-[5-(3-chloro-phenyl)-2-methyl-thiazole-4-carbonyl]-piperidin-3-yl}-amide;
(R)-6-Methyl-imidazo[2,1-b]thiazole-5-carboxylic acid {1-[5-(3-methoxy-phenyl)-2-methyl-thiazole-4-carbonyl]-piperidin-3-yl}-amide;
(R)-6-Methyl-imidazo[2,1-b]thiazole-5-carboxylic acid {1-[5-(2-fluoro-phenyl)-2-methyl-thiazole-4-carbonyl]-piperidin-3-yl}-amide;
(R)-6-Methyl-imidazo[2,1-b]thiazole-5-carboxylic acid {1-[5-(2-chloro-phenyl)-2-methyl-thiazole-4-carbonyl]-piperidin-3-yl}-amide;
(R)-6-Methyl-imidazo[2,1-b]thiazole-5-carboxylic acid {1-[5-(3,4-dimethyl-phenyl)-2-methyl-thiazole-4-carbonyl]-piperidin-3-yl}-amide;
(R)-6-Methyl-imidazo[2,1-b]thiazole-5-carboxylic acid {1-[5-(4-chloro-phenyl)-2-methyl-thiazole-4-carbonyl]-piperidin-3-yl}-amide;
(R)-6-Methyl-imidazo[2,1-b]thiazole-5-carboxylic acid {1-[5-(3,4-difluoro-phenyl)-2-methyl-thiazole-4-carbonyl]-piperidin-3-yl}-amide;
[(R)-3-(5-Bromo-pyrimidin-2-ylamino)-piperidin-1-yl]-[5-(3,4-dimethyl-phenyl)-2 methyl-thiazol-4-yl]-methanone;
Benzofuran-4-carboxylic acid [(R)-1-(biphenyl-2-carbonyl)-piperidin-3-yl]-amide;
6-Methyl-imidazo[2,1-b]thiazole-5-carboxylic acid [(R)-1-(3'-chloro-biphenyl-2-carbonyl)-piperidin-3-yl]-amide; and
6-Methyl-imidazo[2,1-b]thiazole-5-carboxylic acid [(R)-1-(3'-methyl-biphenyl-2-carbonyl)-piperidin-3-yl]-amide;

wherein the first 19 compounds of the above list are especially preferred.

Also part of the invention are compounds of the formula (I) and (Ia) and pharmaceutically acceptable salts thereof.

The term "pharmaceutically acceptable salts" refers to non-toxic, inorganic or organic acid and/or base addition salts. Reference can be made to "Salt selection for basic drugs", *Int. J. Pharm.* (1986), 33, 201-217.

The compounds of formula (I) and (Ia) and their pharmaceutically acceptable salts can be used as medicaments, e.g. in the form of pharmaceutical compositions for enteral or parental administration.

The compounds of the general formula (I) and (Ia) are useful for the treatment and/or prevention of the diseases mentioned herein.

In one embodiment, the invention relates to a method for the treatment and/or prevention of the diseases mentioned herein, said method comprising administering to a subject a pharmaceutically active amount of a compound of general formula I.

The compounds according to general formula (I) and (Ia) may be used for the preparation of a medicament, and are suitable, for the prevention or treatment of diseases selected from the group consisting of dysthymic disorders including major depression and cyclothymia, affective neurosis, manic depression, delirium, psychotic disorders, schizophrenia, delusional paranoia, adjustment disorders and all clusters of personality disorders; anxiety disorders including generalized anxiety, obsessive compulsive disorder, posttraumatic stress disorder, panic attacks, all types of phobic anxiety and avoidance; stress-related syndromes; psychoactive substance use, abuse, seeking and reinstatement; drug abuse; all types of psychological or physical addictions, dissociative disorders including multiple personality syndromes and psychogenic amnesias; sexual dysfunction; psychosexual dysfunction and addiction; tolerance to narcotics or withdrawal from narcotics; hypothalamic-adrenal dysfunctions; disturbed biological and circadian rhythms; all types of sleep disorders; sleep disturbances associated with diseases such as neurological disorders including neuropathic pain and restless leg syndrome; sleep apnea; narcolepsy; insomnias related to psychiatric disorders; all types of idiopathic insomnias and parasomnias; sleep-wake schedule disorders including jet-lag; all dementias and cognitive dysfunctions in the healthy population and in psychiatric and neurologic disorders; mental dysfunctions of aging; severe mental retardation; dyskinesias and muscular diseases; neurodegenerative disorders including Huntington's, Creutzfeld-Jacob's, Alzheimer's diseases and Tourette syndrome; Amyotrophic lateral sclerosis; Parkinson's disease; Cushing's syndrome; traumatic lesions; demyelinating diseases; spinal and cranial nerve diseases; epilepsy; seizure disorders; absence seizures, complex partial and generalized seizures; Lennox-Gastaut syndrome; migraine and headache; pain disorders; anesthesia and analgesia; enhanced or exaggerated sensitivity to pain such as hyperalgesia, causalgia, and allodynia; acute pain; burn pain; atypical facial pain; neuropathic pain; back pain; complex regional pain syndrome I and II; arthritic pain; sports injury pain; pain related to infection e.g. by HIV; post-chemotherapy pain; post-stroke pain; post-operative pain; neuralgia; conditions associated with visceral pain such as irritable bowel syndrome; eating disorders; diabetes; toxic and dysmetabolic disorders including cerebral anoxia, diabetic neuropathies and alcoholism; appetite, taste, eating, or drinking disorders; somatoform disorders including hypochondriasis; vomiting/nausea; inflammatory bowel disease; gastric dyskinesia; gastric ulcers; Kallman's syndrome (anosmia); impaired glucose tolerance; intestinal motility dyskinesias; hypothalamic diseases; hypophysis diseases; idiopathic growth deficiency; dwarfism; gigantism; acromegaly; basophil adenoma; prolactinoma; hyperprolactinemia; brain tumors, adenomas; benign prostatic hypertrophy, prostate cancer; all types of testicular dysfunctions, fertility control; hypothalamic hypogonadism, functional or psychogenic amenorrhea; urinary bladder incontinence asthma; allergies; all types of dermatitis, acne and cysts, sebaceous gland dysfunctions; cardiovascular disorders; heart and lung diseases, acute and congestive heart failure; hypotension; hypertension; urinary retention; osteoporosis; angina pectoris; myocardial infarction; ischemic or haemorrhagic stroke; all types of cerebrovascular disorders including subarachnoid hemorrhage, ischemic and hemorrhagic stroke and vascular dementia; chronic renal failure and other renal diseases; and other diseases related to general orexin system dysfunctions.

Compounds of general formula (I) are particularly suitable for use in the treatment of diseases or disorders selected from the group consisting of all types of sleep disorders, of stress-related syndromes, of psychoactive substance use and abuse, of cognitive dysfunctions in the healthy population and in psychiatric and neurologic disorders, of eating or drinking disorders. Eating disorders may be defined as comprising metabolic dysfunction; dysregulated appetite control; compulsive obesities; emeto-bulimia or anorexia nervosa. Pathologically modified food intake may result from disturbed appetite (attraction or aversion for food); altered energy balance (intake vs. expenditure); disturbed perception of food quality (high fat or carbohydrates, high palatability); disturbed food availability (unrestricted diet or deprivation) or disrupted water balance. Drinking disorders include polydipsias in psychiatric disorders and all other types of excessive fluid intake. Sleep disorders include all types of insomnias, narcolepsy and other disorders of excessive sleepiness, sleep-related dystonias; restless leg syndrome; sleep apneas; jet-lag syndrome; shift-work syndrome, delayed or advanced sleep phase syndrome or insomnias related to psychiatric disorders. Insomnias are defined as comprising sleep disorders associated with aging; intermittent treatment of chronic insomnia; situational transient insomnia (new environment, noise) or short-term insomnia due to stress; grief; pain or illness. Insomnia also include stress-related syndromes including post-traumatic stress disorders as well as other types and subtypes of anxiety disorders such as generalized anxiety, obsessive compulsive disorder, panic attacks and all types of phobic anxiety and avoidance; psychoactive substance use, abuse, seeking and reinstatement are defined as all types of psychological or physical addictions and their related tolerance and dependence components. Cognitive dysfunctions include deficits in all types of attention, learning and memory functions occurring transiently or chronically in the normal, healthy, young, adult or aging population, and also occurring transiently or chronically in psychiatric, neurologic, cardiovascular and immune disorders.

In a further preferred embodiment of the invention compounds of general formula (I) are particularly suitable for use in the treatment of diseases or disorders selected from the group consisting of sleep disorders that comprises all types of insomnias, narcolepsy and other disorders of excessive sleepiness, sleep-related dystonias, restless leg syndrome, sleep apneas, jet-lag syndrome, shift-work syndrome, delayed or advanced sleep phase syndrome or insomnias related to psychiatric disorders.

In another preferred embodiment of the invention compounds of general formula (I) and (Ia) are particularly suitable for use in the treatment of diseases or disorders selected from the group consisting of cognitive dysfunctions that comprise deficits in all types of attention, learning and memory functions occurring transiently or chronically in the normal, healthy, young, adult or aging population, and also occurring transiently or chronically in psychiatric, neurologic, cardiovascular and immune disorders.

In another preferred embodiment of the invention compounds of general formula (I) and (Ia) are particularly suitable for use in the treatment of diseases or disorders selected from the group consisting of eating disorders that comprise metabolic dysfunction; dysregulated appetite control; compulsive obesities; emeto-bulimia or anorexia nervosa.

In another preferred embodiment of the invention compounds of general formula (I) and (Ia) are particularly suitable for use in the treatment of diseases or disorders selected from the group consisting of psychoactive substance use and abuse that comprise all types of psychological or physical addictions and their related tolerance and dependence components.

The production of the pharmaceutical compositions can be effected in a manner which will be familiar to any person skilled in the art (see for example Remington, *The Science and Practice of Pharmacy*, 21st Edition (2005), Part 5, "Pharmaceutical Manufacturing" [published by Lippincott Williams & Wilkins]) by bringing the described compounds of Formula (I) or their pharmaceutically acceptable salts, optionally in combination with other therapeutically valuable substances, into a galenical administration form together with suitable, non-toxic, inert, therapeutically compatible solid or liquid carrier materials and, if desired, usual pharmaceutical adjuvants.

Unless used regarding temperatures, the term "about" placed before a numerical value "X" refers in the current application to an interval extending from X minus 10% of X to X plus 10% of X, and preferably to an interval extending from X minus 5% of X to X plus 5% of X. In the particular case of temperatures, the term "about" placed before a temperature "Y" refers in the current application to an interval extending from the temperature Y minus 10° C. to Y plus 10° C., and preferably to an interval extending from Y minus 5° C. to Y plus 5° C. Besides, the term "room temperature" (rt) as used herein refers to a temperature of about 25° C.

Preparation of Compounds of Formula (I)

A further aspect of the invention is a process for the preparation of compounds of formula (I) and (Ia). Compounds according to formula (I) and (Ia) of the present invention can be prepared according to the general sequence of reactions outlined in the schemes below wherein A, B, X, and $R^1$ are as defined in the description for formula (I) and (Ia). Additional generic groups as used in the schemes below are defined as followed: R represents hydrogen, $(C_{1-4})$alkyl or halogen; $R^1$ represents hydrogen or $(C_{1-4})$alkyl; and R" represents hydrogen, $(C_{1-4})$alkyl, $(C_{1-4})$alkoxy, trifluoromethyl, cyano or halogen. The compounds obtained may also be converted into pharmaceutically acceptable salts thereof in a manner known per se.

The compounds of formula (I) and (Ia) wherein X—$R^1$ represents —N(H)-pyrimidinyl (especially in case $R^1$ is a pyrimidin-2-yl moiety) may be prepared starting from the commercially available (+/−)-3-amino-1-N-Boc-piperidine (1) or from enantiomerically pure (R)-3-amino-1-N-Boc-piperidine by reaction with the corresponding commercially available 2-chloro-pyrimidine derivative under basic conditions such as $K_2CO_3$ in presence of DIEA in a solvent such as xylene at reflux. The resulting amine intermediate (2) is transformed to compounds (3) by cleavage under acidic conditions of the Boc protecting group such as TFA in DCM followed by amid formation with the respective carboxylic acid B-A-$CO_2H$ using standard amide coupling techniques such as PyBOP in presence of DIEA in a solvent such as DMF (scheme 1).

Scheme 1: Synthesis of compounds of formula (I) wherein
X—$R^1$ represents —N(H)-pyrimidin-2-yl

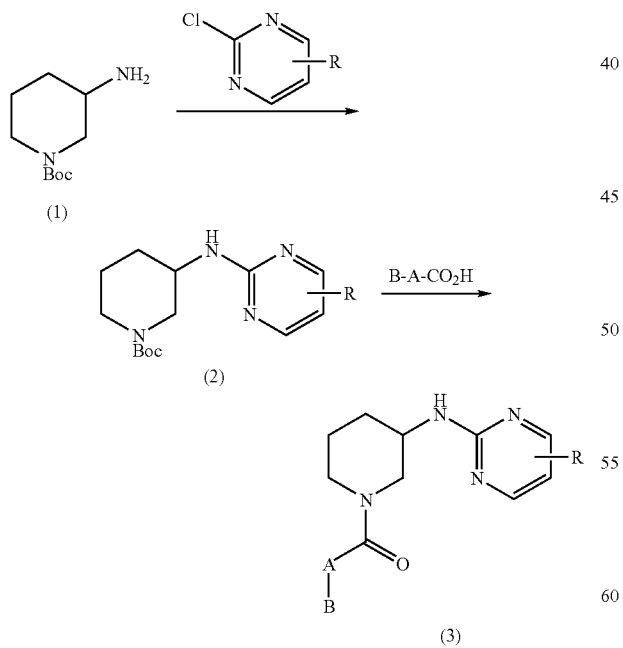

The compounds of formula (I) and (Ia), wherein X—$R^1$ represents —NH—C(O)-heterocyclyl may be prepared starting from the commercially available (+/−)-3-amino-1-N-Boc-piperidine (1) or from enantiomerically pure (R)-3-amino-1-N-Boc-piperidine by reaction with the respective carboxylic acid derivative $R^1$—$CO_2H$ using standard amide coupling techniques as above. The resulting amide intermediates (4) are transformed to compounds (5) by cleavage of the Boc protecting group as described above, followed by amide formation with the respective carboxylic acid B-A-$CO_2H$ (scheme 2) as described above.

Scheme 2: Synthesis of compounds of formula (I) and/or (Ia), wherein X—$R^1$ represents —NH—C(O)-heterocyclyl

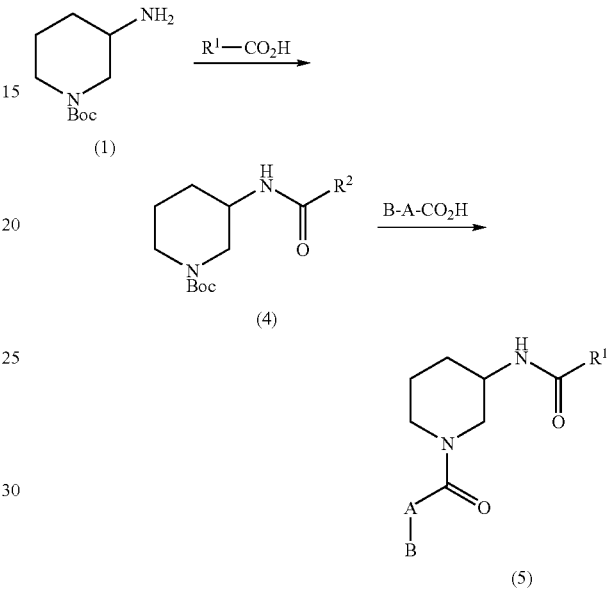

Preparation of Carboxylic Acids B-A-$CO_2H$

Carboxylic acid derivatives B-A-$CO_2H$ wherein B-A represents a 5-phenyl-thiazole-4-yl derivative are commercially available or can be synthesised according to scheme 3.

Scheme 3: Synthesis of carboxylic acids B-A-$CO_2H$ wherein B-A represents a 5-phenyl-thiazole-4-yl derivative

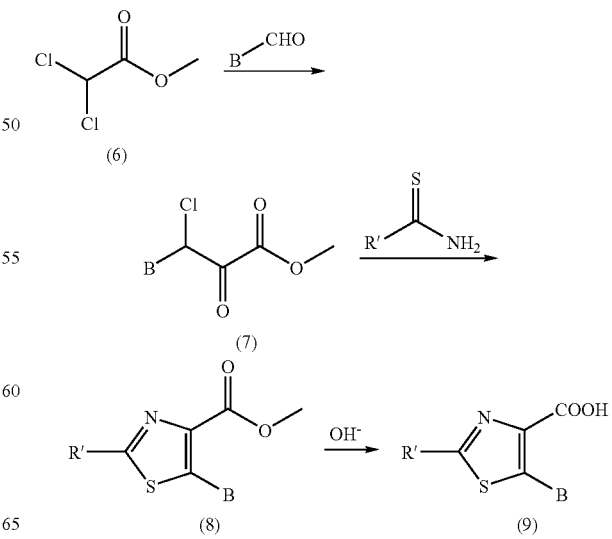

By reaction of methyl dichloroacetate (6) with commercially available benzaldehyde derivatives B—CHO in the presence of a base such as KOtBu in an aprotic polar solvent such as THF at RT 3-chloro-2-oxo-propionic acid ester derivatives (7) are obtained (Hamamoto H. et al Tetrahedron *Asymmetry* 2000, 11, 4485-4497). Compounds of structure (7) can be transformed by reaction with commercially available thioamides at RT in solvents such as MeCN to provide thiazol-4-carboxylic acid ester derivatives (8) (U.S. Pat. No. 3,282, 927). Saponification of the ester function using methods known in the art such as treatment with a base such as NaOH in a solvent such as MeOH provides the corresponding 5-phenyl-thiazol-4-carboxylic acid derivatives (9). The respective benzaldehydes are commercially available or well known in the art. Thioamides of formula R'—C(S)—$NH_2$, wherein R' represents ($C_{1-4}$)alkyl are commercially available or, alternatively, can be synthesized from commercially available carboxamides with Lawesson's reagent.

Carboxylic acid derivatives B-A-$CO_2$H wherein B-A represents a 4-phenyl-thiazole-5-yl derivative are commercially available or synthesised according to scheme 4.

Scheme 4: Synthesis of carboxylic acids B-A-$CO_2$H wherein B-A represents a 4-phenyl-thiazole-5-yl derivative

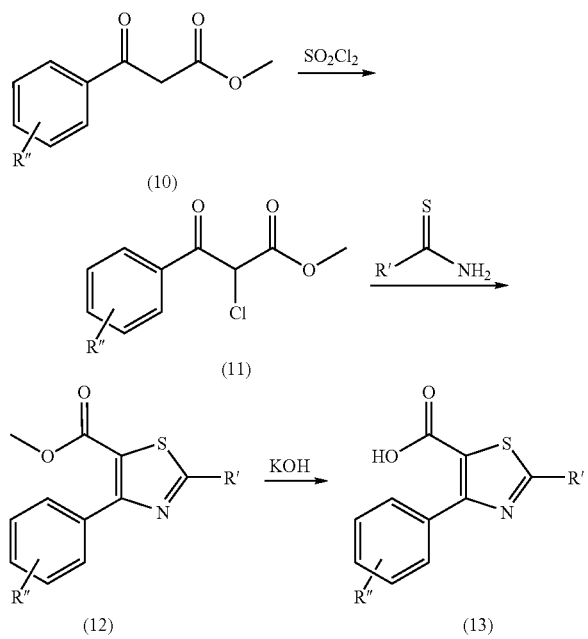

By refluxing a commercially available 3-oxo-propionic acid ester derivative (10) with $SO_2Cl_2$ in a solvent such as $CHCl_3$ the corresponding 2-chloro-3-oxo-propionic acid ester derivatives (11) can be obtained. Compounds of structure (11) can be transformed by reaction with commercially available thioamides R'—C(S)—$NH_2$ at reflux temperature in solvents such as THF in presence of a base such as $NaHCO_3$ to the corresponding thiazol-5-carboxylic acid ester derivatives (12). Saponification of the ester function using methods known in the art such as treatment with a base such as KOH in a solvent such as ethanol provides the corresponding 4-phenyl-thiazol-5-carboxylic acid derivatives (13).

Carboxylic acid derivatives B-A-$CO_2$H wherein B-A represents a biphen-2-yl derivative are commercially available or can be synthesised according to scheme 5.

Scheme 5: Synthesis of carboxylic acids B-A-$CO_2$H wherein B-A represents a biphen-2-yl derivative

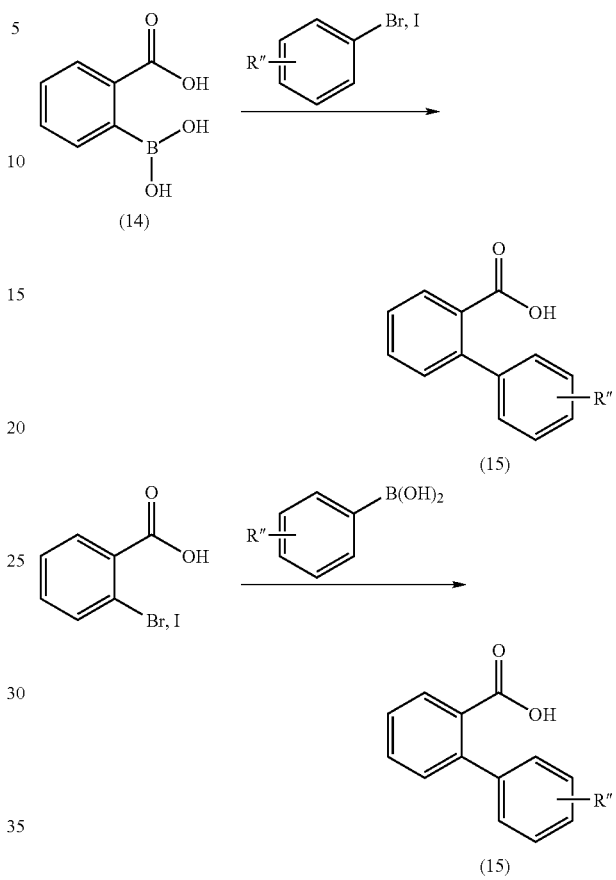

Reaction of commercially available (2-carboxyphenyl)-boronic acid derivatives (14) or esters thereof with commercially available phenyl-bromides or phenyl-iodides in presence of a catalyst such as Pd($PPh_3$)$_4$ and a base such as $Na_2CO_3$ under heating in a solvent such as toluene, dioxane, THF provides, after saponification, if needed, of the ester using well known methods, the corresponding biphenyl-2-carboxylic acid derivatives (15). Alternatively, reaction of commercially available 2-bromo-, or 2-iodo-benzoic acid, or esters thereof, with commercially available phenyl-boronic acid derivatives using the conditions described before provides the corresponding biphenyl-2-carboxylic acid derivatives (15).

Synthesis of Carboxylic Acids $R^1$—COOH

Carboxylic acids of formula $R^1$—$CO_2$H are commercially available or well known in the art (Lit. e.g. WO2001/096302; T. Eicher, S. Hauptmann "The chemistry of Heterocycles: Structure, Reactions, Syntheses, and Applications", 2nd Edition 2003, Wiley, ISBN 978-3-527-30720-3).

Carboxylic acid derivatives $R^1$—$CO_2$H which represent an imidazo[2,1-b]thiazole-carboxylic acid derivative are commercially available, or can be synthesised according to the literature according to scheme 6.

Scheme 6: Synthesis of carboxylic acids $R^1$—$CO_2H$ which represent an imidazo[2,1-b]thiazole-carboxylic acid derivative Pathway A

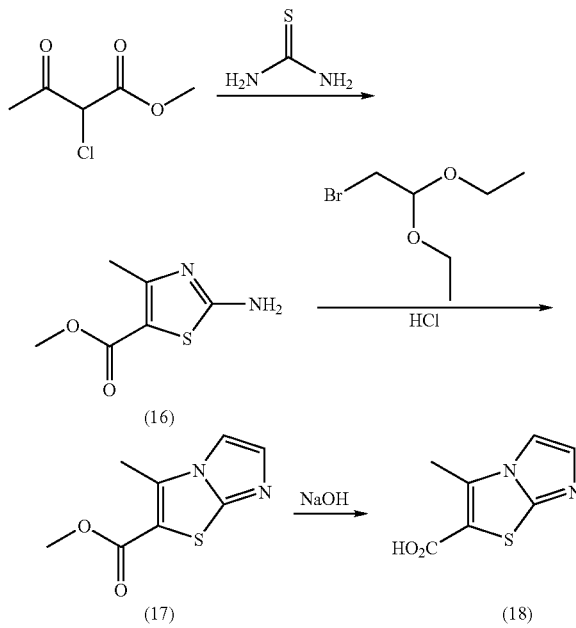

Pathway B

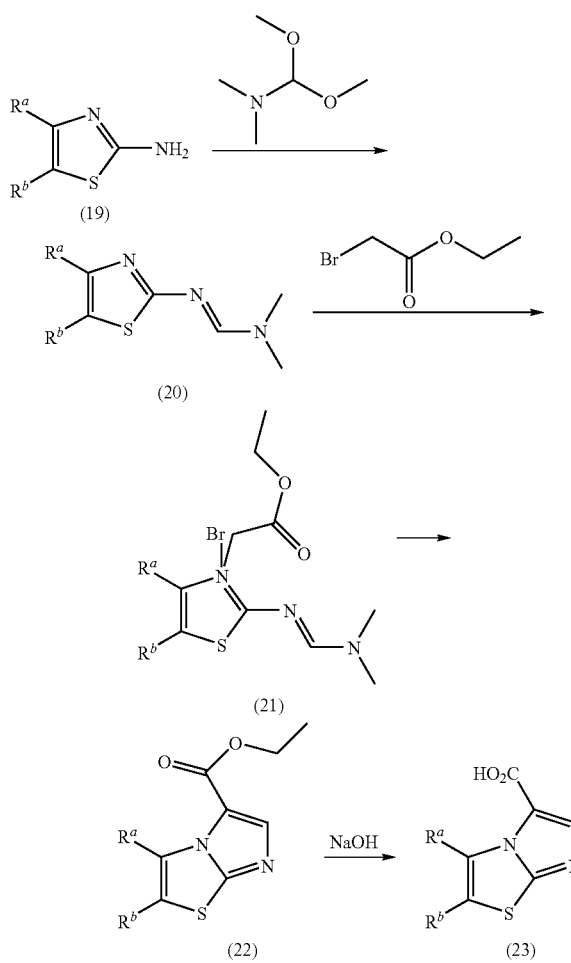

Pathway C

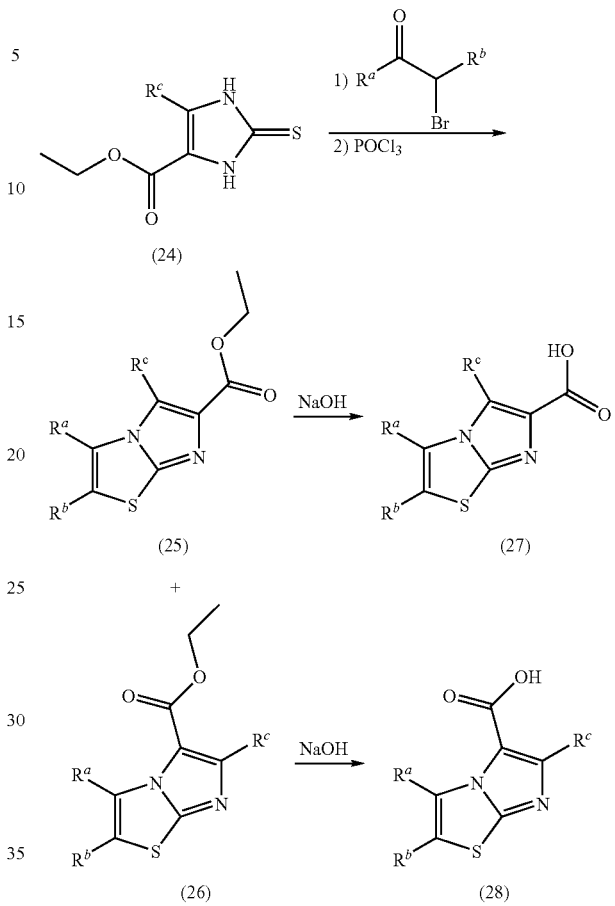

Pathway A: By reaction of commercially available 2-chloro-3-oxo-butyric acid methyl ester with thiourea the amino-thiazole (16) can be obtained. Transformation to ester (17) can be accomplished with bromoacetaldehyde which can be generated in-situ from bromoacetaldehyde diethylacetal under acidic conditions. After saponification with bases such as sodium hydroxide the desired acid (18) can be obtained (WO02/46158)

Pathway B: By heating an commercially available aminothiazole derivative of structure (19) with N,N-dimethylformamide dimethylacetal in a solvent such as toluene formamidine derivatives (20) can be obtained. They can be alkylated with ethyl bromoacetate yielding the respective thiazolium bromide (21) which can be cyclised with strong bases such as DBU to the ester (22). Saponification of the ester function using methods known in the art such as treatment with a base such as NaOH in a solvent such as ethanol/water provides the corresponding imidazo[2,1-b]thiazole-5-carboxylic acid derivatives (23) (WO95/29922 and U.S. Pat. No. 6,191,124).

Pathway C: By reaction of a 4-ethoxycarbonylimidazo-2-thiol derivative (24) with a bromo-ketone derivative in EtOH followed by cyclisation with $POCl_3$ to yield a mixture of the two regioisomeric ester derivatives (25) and (26) which can be separated by FC. Saponification with a base such as NaOH in a solvent such as ethanol/water provide the desired imidazo[2,1-b]thiazole carboxylic acids (27) and (33) (U.S. Pat. No. 4,267,339 and DE2505068). 4-Ethoxycarbonylimidazo-2-thiol derivatives (24) are commercially available or, alternatively, can be synthesized from the corresponding commercially available imidazolones with Latvesson's reagent. Alternatively, acids of structure (28) wherein $R^c$ represents methyl can be synthesized by alkylating and cyclizing compounds of structure (19) with bromoacetone, followed by formylation of the obtained imidazo[2,1-b]thiazole in position 5 with $POCl_3$/DMF and oxidation of the obtained aldehyde to the corresponding carboxylic acid according to well known methods. In scheme 6 preferably $R^a$, $R^b$ and $R^c$ independently represent hydrogen or methyl.

Whenever the compounds of formula (I) are obtained in the form of mixtures of enantiomers, the enantiomers can be separated using methods known to one skilled in the art: e.g. by formation and separation of diastereomeric salts or by HPLC over a chiral stationary phase such as a Regis Whelk-O1(R,R) (10 μm) column, a Daicel ChiralCel OD-H (5-10 μm) column, or a Daicel ChiralPak IA (10 μm) or AD-H (5 μm) column. Typical conditions of chiral HPLC are an isocratic mixture of eluent A (EtOH, in presence or absence of an amine such as triethylamine, diethylamine) and eluent B (hexane), at a flow rate of 0.8 to 150 mL/min.

EXPERIMENTAL SECTION

Abbreviations (as Used Herein and in the Description Above):

| | |
|---|---|
| Boc | tert-butoxycarbonyl |
| BSA | Bovine serum albumine |
| CHO | Chinese hamster ovary |
| conc | Concentrated |
| d | day(s) |
| DBU | Diaza(1,3)bicyclo[5.4.0]undecane |
| DCM | Dichloromethane |
| DIEA | Disopropylethylamine |
| DMF | N,N-dimethylformamide |
| DMSO | Dimethyl sulfoxide |
| EA | Ethyl acetate |
| eq | Equivalent(s) |
| ES | Electron spray |
| ether | Diethylether |
| FC | Flash chromatography |
| FCS | Foatal calf serum |
| FLIPR | Fluorescent imaging plate reader |
| h | Hour(s) |
| HBSS | Hank's balanced salt solution |
| HEPES | 4-(2-hydroxyethyl)-piperazine-1-ethanesulfonic acid |
| HPLC | High performance liquid chromatography |
| LC | Liquid chromatography |
| M | Molar(ity) |
| MeOH | Methanol |
| min | Minute(s) |
| MS | Mass spectroscopy |
| Ph | phenyl |
| PyBOP | (Benzotriazole-lyloxy)-tripyrrolidinophosphonium-hexafluorophosphate |
| RT | Room temperature |
| sat | saturated |
| THF | Tetrahydrofuran |
| TFA | Trifluoroacetic acid |
| $t_R$ | Retention time |

I-Chemistry

The following examples illustrate the preparation of pharmacologically active compounds of the invention but do not at all limit the scope thereof.

All temperatures are stated in ° C.

All the analytical HPLC investigations on non-chiral phases are performed using RP—$C_{18}$ based columns. Analytical HPLC investigations are performed on an instrument with cycle-times of ~2.5 min. NMR measurements are done with a Bruker Avance 400 Instrument.

A. Preparation of Precursors and Intermediates

A.1 Synthesis of Thiazole-4-Carboxylic Acid Derivatives

A.1.1 Synthesis Of 3-Chloro-2-Oxo-Propionic Ester Derivatives (General Procedure)

A solution of the respective aldehyde B—CHO (338 mmol, 1.0 eq) and methyl dichloroacetate (338 mmol, 1.0 eq) in THF (100 mL) is added dropwise to a cold (−60° C.) suspension of KOtBu (335 mmol, 1.0 eq) in THF (420 mL). After 4 h the mixture is allowed to reach RT, stirred over night and concentrated in vacuo. DCM and ice-cold water are added, the layers are separated and the aqueous layer is extracted twice with DCM. The combined organic layers are washed with ice-cold water and brine, dried over $MgSO_4$ and concentrated in vacuo to give the desired t-oxo-propionic acid ester which is used without further purification.

3-chloro-2-oxo-3-m-tolyl-propionic acid methyl ester prepared by reaction of 3-methyl-benzaldehyde with methyl dichloroacetate.

3-chloro-2-oxo-3-p-tolyl-propionic acid methyl ester prepared by reaction of 4-methyl-benzaldehyde with methyl dichloroacetate.

3-chloro-3-(4-ethyl-phenyl)-2-oxo-propionic acid methyl ester prepared by reaction of 4-ethyl-benzaldehyde with methyl dichloroacetate.

3-chloro-3-(3-fluoro-phenyl)-2-oxo-propionic acid methyl ester prepared by reaction of 3-fluoro-benzaldehyde with methyl dichloroacetate.

3-chloro-3-(4-fluoro-phenyl)-2-oxo-propionic acid methyl ester prepared by reaction of 4-fluoro-benzaldehyde with methyl dichloroacetate.

3-chloro-3-(4-trifluoromethyl-phenyl)-2-oxo-propionic acid methyl ester prepared by reaction of 4-trifluoromethyl-benzaldehyde with methyl dichloro-acetate.

3-chloro-3-(2-fluoro-phenyl)-2-oxo-propionic acid methyl ester prepared by reaction of 2-fluoro-benzaldehyde with methyl dichloro-acetate.

3-chloro-3-(2-chloro-phenyl)-2-oxo-propionic acid methyl ester prepared by reaction of 2-chloro-benzaldehyde with methyl dichloro-acetate.

3-chloro-3-(3-chloro-phenyl)-2-oxo-propionic acid methyl ester prepared by reaction of 3-chloro-benzaldehyde with methyl dichloro-acetate.

3-chloro-2-oxo-3-o-tolyl-propionic acid methyl ester prepared by reaction of 2-methyl-benzaldehyde with methyl dichloro-acetate.

3-chloro-3-(2-methoxy-phenyl)-2-oxo-propionic acid methyl ester prepared by reaction of 2-methoxy-benzaldehyde with methyl dichloro-acetate.

3-chloro-3-(3-methoxy-phenyl)-2-oxo-propionic acid methyl ester prepared by reaction of 3-methoxy-benzaldehyde with methyl dichloro-acetate.

3-chloro-2-oxo-3-(2-trifluoromethyl-phenyl)-propionic acid methyl ester prepared by reaction of 2-trifluoromethyl-benzaldehyde with methyl dichloro-acetate.

3-chloro-2-oxo-3-(3-trifluoromethyl-phenyl)-propionic acid methyl ester prepared by reaction of 3-trifluoromethyl-benzaldehyde with methyl dichloro-acetate.

3-chloro-3-(3,4-dimethyl-phenyl)-2-oxo-propionic acid methyl ester prepared by reaction of 3,4-dimethyl-benzaldehyde with methyl dichloro-acetate.

A.1.2 Synthesis of Thiazole-4-Carboxylic Acid Methyl Ester Derivatives (General Procedure)

A solution of thioacetamide (132 mmol, 1.0 eq) in MeCN (250 mL) is added to a mixture of the respective 2-oxo-propionic acid ester (132 mmol, 1.0 eq) and molecular sieves (4 Å, 12 g) in MeCN (60 mL). After stifling for 5 h the mixture is cooled in an ice-bath and the obtained precipitate is filtered off. The residue is washed with cold MeCN, dried, dissolved in MeOH (280 mL) and stirred at 50° C. for 6 h. The solvents are removed in vacuo to give the desired thiazole derivatives as a white solid.

2-methyl-5-m-tolyl-thiazole-4-carboxylic acid methyl ester prepared by reaction of 3-chloro-2-oxo-3-m-tolyl-propionic acid methyl ester with thioacetamide. LC-MS: $t_R$=0.94 min; $[M+H]^+$=248.0.

2-methyl-5-p-tolyl-thiazole-4-carboxylic acid methyl ester prepared by reaction of 3-chloro-2-oxo-3-p-tolyl-propionic acid methyl ester with thioacetamide. LC-MS: $t_R$=0.92 min; $[M+H]^+$=248.2.

5-(4-ethyl-phenyl)-2-methyl-thiazole-4-carboxylic acid methyl ester prepared by reaction of 3-chloro-3-(4-ethyl-phenyl)-2-oxo-propionic acid methyl ester with thioacetamide. LC-MS: $t_R$=0.98 min; $[M+H]^+$=262.1.

5-(3-fluoro-phenyl)-2-methyl-thiazole-4-carboxylic acid methyl ester prepared by reaction of 3-chloro-3-(3-fluoro-phenyl)-2-oxo-propionic acid methyl ester with thioacetamide. LC-MS: $t_R$=0.91 min; $[M+H]^+$=252.1.

5-(4-fluoro-phenyl)-2-methyl-thiazole-4-carboxylic acid methyl ester prepared by reaction of 3-chloro-3-(4-fluoro-phenyl)-2-oxo-propionic acid methyl ester with thioacetamide.
$^1$H-NMR (CDCl$_3$): δ=2.75 (s, 3H); 3.84 (s, 3H); 7.10 (m, 2H); 7.47 (m, 2H).

2-methyl-5-(4-trifluoromethyl-phenyl)-thiazole-4-carboxylic acid methyl ester prepared by reaction of 3-chloro-3-(4-trifluoromethyl-phenyl)-2-oxo-propionic acid methyl ester with thioacetamide. LC-MS: $t_R$=0.98 min; $[M+H]^+$=302.0.

2-methyl-5-(3-trifluoromethyl-phenyl)-thiazole-4-carboxylic acid methyl ester prepared by reaction of 3-chloro-3-(3-trifluoromethyl-phenyl)-2-oxo-propionic acid methyl ester with thioacetamide. LC-MS: $t_R$=0.98 min; $[M+H]^+$=302.2.

2-methyl-5-(2-trifluoromethyl-phenyl)-thiazole-4-carboxylic acid methyl ester prepared by reaction of 3-chloro-3-(2-trifluoromethyl-phenyl)-2-oxo-propionic acid methyl ester with thioacetamide. LC-MS: $t_R$=0.94 min; $[M+H]^+$=302.3.

5-(2-fluoro-phenyl)-2-methyl-thiazole-4-carboxylic acid methyl ester prepared by reaction of 3-chloro-3-(2-fluoro-phenyl)-2-oxo-propionic acid methyl ester with thioacetamide. LC-MS: $t_R$=0.89 min; $[M+H]^+$=252.0.

5-(2-chloro-phenyl)-2-methyl-thiazole-4-carboxylic acid methyl ester prepared by reaction of 3-chloro-3-(2-chloro-phenyl)-2-oxo-propionic acid methyl ester with thioacetamide. LC-MS: $t_R$=0.92 min; $[M+H]^+$=268.0.

5-(3-chloro-phenyl)-2-methyl-thiazole-4-carboxylic acid methyl ester prepared by reaction of 3-chloro-3-(3-chloro-phenyl)-2-oxo-propionic acid methyl ester with thioacetamide. LC-MS: $t_R$=0.95 min; $[M+H]^+$=268.0.

2-methyl-5-o-tolyl-thiazole-4-carboxylic acid methyl ester prepared by reaction of 3-chloro-2-oxo-3-o-tolyl-propionic acid methyl ester with thioacetamide. LC-MS: $t_R$=0.92 min; $[M+H]^+$=248.1.

5-(2-methoxy-phenyl)-2-methyl-thiazole-4-carboxylic acid methyl ester prepared by reaction of 3-chloro-3-(2-methoxy-phenyl)-2-oxo-propionic acid methyl ester with thioacetamide. LC-MS: $t_R$=0.88 min; $[M+H]^+$=264.1.

5-(3-methoxy-phenyl)-2-methyl-thiazole-4-carboxylic acid methyl ester prepared by reaction of 3-chloro-3-(3-methoxy-phenyl)-2-oxo-propionic acid methyl ester with thioacetamide. LC-MS: $t_R$=0.90 min; $[M+H]^+$=263.9.

5-(3,4-dimethyl-phenyl)-2-methyl-thiazole-4-carboxylic acid methyl ester prepared by reaction of 3-chloro-3-(3,4-dimethyl-phenyl)-2-oxo-propionic acid methyl ester with thioacetamide. LC-MS: $t_R$=0.96 min; $[M+H]^+$=262.3.

A.1.3 Synthesis of Thiazole-4-Carboxylic Acid Derivatives (General Procedure)

A solution of the respective thiazole-4-carboxylic acid ester derivative (96.2 mmol) in a mixture of THF (150 mL) and MeOH (50 mL) is treated with an aqueous NaOH solution (1.0 M, 192 mL). After stirring for 3 h a white suspension is formed and the organic volatiles are removed in vacuo. The remaining mixture is diluted with water (100 mL), cooled in an ice-bath and made acidic (pH=3-4) by addition of aqueous HCl solution (1.0 M). The suspension is filtered and the residue is washed with cold water. After drying the desired acid is obtained as a white solid.

2-methyl-5-m-tolyl-thiazole-4-carboxylic acid prepared by saponification of 2-methyl-5-m-tolyl-thiazole-4-carboxylic acid methyl ester. LC-MS: $t_R$=0.83 min; $[M+H]^+$=234.0.

2-methyl-5-p-tolyl-thiazole-4-carboxylic acid prepared by saponification of 2-methyl-5-p-tolyl-thiazole-4-carboxylic acid methyl ester. LC-MS: $t_R$=0.83 min; $[M+H]^+$=234.0.

5-(4-ethyl-phenyl)-2-methyl-thiazole-4-carboxylic acid prepared by saponification of 5-(4-ethyl-phenyl)-2-methyl-thiazole-4-carboxylic acid methyl ester. LC-MS: $t_R$=0.88 min; $[M+H]^+$=248.0.

5-(3-fluoro-phenyl)-2-methyl-thiazole-4-carboxylic acid prepared by saponification of 5-(3-fluoro-phenyl)-2-methyl-thiazole-4-carboxylic acid methyl ester. LC-MS: $t_R$=0.82 min; $[M+H]^+$=238.1.

5-(4-fluoro-phenyl)-2-methyl-thiazole-4-carboxylic acid prepared by saponification of 5-(4-fluoro-phenyl)-2-methyl-thiazole-4-carboxylic acid methyl ester. $^1$H-NMR (DMSO-$d_6$): δ=2.67 (s, 3H); 7.27 (m, 2H); 7.53 (m, 2H); 12.89 (br.s, 1H).

2-methyl-5-(4-trifluoromethyl-phenyl)-thiazole-4-carboxylic acid prepared by saponification of 2-methyl-5-(4-trifluoromethyl-phenyl)-thiazole-4-carboxylic acid methyl ester. LC-MS: $t_R$=0.90 min; $[M+H]^+$=288.0.

2-methyl-5-(3-trifluoromethyl-phenyl)-thiazole-4-carboxylic acid prepared by saponification of 2-methyl-5-(3-trifluoromethyl-phenyl)-thiazole-4-carboxylic acid methyl ester. LC-MS: $t_R$=0.88 min; $[M+H]^+$=288.0.

2-methyl-5-(2-trifluoromethyl-phenyl)-thiazole-4-carboxylic acid prepared by saponification of 2-methyl-5-(2-trifluoromethyl-phenyl)-thiazole-4-carboxylic acid methyl ester. LC-MS: $t_R$=0.84 min; $[M+H]^+$=288.3.

5-(2-fluoro-phenyl)-2-methyl-thiazole-4-carboxylic acid prepared by saponification of 5-(2-fluoro-phenyl)-2-methyl-thiazole-4-carboxylic acid methyl ester. LC-MS: $t_R$=0.78 min; $[M+H]^+$=238.3.

5-(2-chloro-phenyl)-2-methyl-thiazole-4-carboxylic acid prepared by saponification of 5-(2-chloro-phenyl)-2-methyl-thiazole-4-carboxylic acid methyl ester. LC-MS: $t_R$=0.82 min; $[M+H]^+$=253.9.

5-(3-chloro-phenyl)-2-methyl-thiazole-4-carboxylic acid prepared by saponification of 5-(3-chloro-phenyl)-2-methyl-thiazole-4-carboxylic acid methyl ester. LC-MS: $t_R$=0.84 min; $[M+H]^+$=254.0.

2-methyl-5-o-tolyl-thiazole-4-carboxylic acid prepared by saponification of 2-methyl-5-o-tolyl-thiazole-4-carboxylic acid methyl ester. LC-MS: $t_R$=0.80 min; $[M+H]^+$=234.3.

5-(3-methoxy-phenyl)-2-methyl-thiazole-4-carboxylic acid prepared by saponification of 5-(3-methoxy-phenyl)-2-methyl-thiazole-4-carboxylic acid methyl ester. LC-MS: $t_R$=0.80 min; [M+H]$^+$=250.0.

5-(2-methoxy-phenyl)-2-methyl-thiazole-4-carboxylic acid prepared by saponification of 5-(2-methoxy-phenyl)-2-methyl-thiazole-4-carboxylic acid methyl ester. LC-MS: $t_R$=0.78 min; [M+H]$^+$=250.0.

5-(3,4-dimethyl-phenyl)-2-methyl-thiazole-4-carboxylic acid prepared by saponification of 5-(3,4-dimethyl-phenyl)-2-methyl-thiazole-4-carboxylic acid methyl ester. LC-MS: $t_R$=0.86 min; [M+H]$^+$=248.3.

A.2 Synthesis of 3-(N-substituted)-piperidine-1-carboxylic acid tert-butyl ester A.2.1 Synthesis of 3-(5-bromo-pyrimidin-2-ylamino)-piperidine-1-carboxylic acid tert-butyl ester To a solution of (+/−)-3-amino-1-N-Boc-piperidine (1 g) in dry o-xylene (20 mL) were added successively 5-bromo-2-chloropyrimidine (965 mg), anhydrous K$_2$CO$_3$ (1.38 g), DIEA (3.42 mL). The reaction mixture was stirred at reflux for 3 d under nitrogen. After cooling to RT, the brown suspension was filtered and the filtrate was concentrated to yield a crude brown-orange oil. FC (EA/n-heptane: 3/7) gave 850 mg (46%) of the title compound as a light brown solid.
LC-MS: $t_R$=0.98 min; [M+H]$^+$=358.

A.2.2 Synthesis of (R)-3-(5-bromo-pyrimidin-2-ylamino)-piperidine-1-carboxylic acid tert-butyl ester To a solution of (R)-3-amino-1-N-Boc-piperidine (920 mg) in dry EtOH (20 mL) were added successively 5-bromo-2-chloropyrimidine (957 mg), DIEA (0.86 mL). The reaction mixture was stirred at reflux for 16 hours under nitrogen. After cooling to RT, the reaction mixture was diluted with EA, washed with sat. NaHCO$_3$, 1N NaOH. The organic extract was dried (MgSO$_4$), filtered and concentrated to yield a crude brown-orange oil. FC (EA/n-heptane: 2/8) gave 787 mg (48%) of the title compound as a light brown solid.
LC-MS: $t_R$=0.98 min; [M+H]$^+$=358.

A.2.3 Synthesis of (R)-3-[(6-methyl-imidazo[2,1-b]thiazole-5-carbonyl)-amino]-piperidine-1-carboxylic acid tert-butyl ester A mixture of (R)-3-amino-1-N-Boc-piperidine (800 mg), 6-methyl-imidazo[2,1-b]thiazole-5-carboxylic acid (801.5 mg), PyBOP (2.08 g), DIEA (1.57 mL) in dry DMF (10 mL) was stirred at RT under nitrogen for 20 h. The reaction mixture was diluted with EA, washed with water. The aqueous phase was extracted twice with EA, the combined organic extracts were washed with brine, dried (MgSO$_4$), filtered and concentrated to yield a crude light brown oil. FC (EA/n-heptane: 1/1 to EA) gave 1.47 g (100%) of the title compound as a solid.
LC-MS: $t_R$=0.78 min; [M+H]$^+$=365.

A.2.4 Synthesis of (R)-3-[(benzofuran-4-carbonyl)-amino]-piperidine-1-carboxylic acid tert-butyl ester A mixture of (R)-3-amino-1-N-Boc-piperidine (1 g), benzofuran-4-carboxylic acid (809 mg), PyBOP (2.6 g), DIEA (1.96 mL) in dry DMF (10 mL) was stirred at RT under nitrogen for 20 h. The reaction mixture was diluted with EA, washed with water. The aqueous phase was extracted twice with EA, the combined organic extracts were washed with brine, dried (MgSO$_4$), filtered and concentrated to yield a crude light brown oil. FC (EA/n-heptane: 1/1 to EA) gave 1.41 g (82%) of the title compound as an oil.
LC-MS: $t_R$=0.93 min; [M+H]$^+$=345.
(RS)-3-[(benzofuran-4-carbonyl)-amino]-piperidine-1-carboxylic acid tert-butyl ester is synthesized in analogy from (+/−)-3-amino-1-N-Boc-piperidine.

A.3 Synthesis of 3-(N-Substituted)-Piperidine Derivatives

A.3.1 Synthesis of (5-bromo-pyrimidin-2-yl)-piperidin-3-ylamine

To a cold (~0° C.) solution of 3-(5-bromo-pyrimidin-2-ylamino)-piperidine-1-carboxylic acid tert-butyl ester (850 mg) in dry DCM (10 mL) was added slowly TFA (0.911 mL). The reaction mixture was stirred at RT for 20 h, 5 eq more of TFA (0.911 mL) was added and the stirring was continued for 2 h. The reaction was concentrated in vacuo to yield the title compound as a bis-trifluoroacetate salt, which was used for the next step without further purification.
LC-MS: $t_R$=0.56 min; [M]$^+$=257

A.3.2 Synthesis of (R)-(5-bromo-pyrimidin-2-yl)-piperidine-3-yl-amine

To a cold (~0° C.) solution of (R)-3-(5-bromo-pyrimidin-2-ylamino)-piperidine-1-carboxylic acid tert-butyl ester (775 mg) in dry DCM (10 mL) was added slowly TFA (0.831 mL). The reaction mixture was stirred at RT for 20 h, 5 eq more of TFA (0.831 mL) was added and the stirring was continued for 2 h. The reaction was concentrated in vacuo to yield the title compound as a bis-trifluoroacetate salt which was used for the next step without further purification.
LC-MS: $t_R$=0.56 min; [M]$^+$=257.

A.3.3 Synthesis of (R)-6-methyl-imidazo[2,1-b]-thiazole-5-carboxylic acid-piperidin-3-ylamide To a cold (~0° C.) solution of (R)-3-[(6-methyl-imidazo[2,1-b]thiazole-5-carbonyl)-amino]-piperidine-1-carboxylic acid tent-butyl ester (1.47 g) in dry DCM (30 mL) was added slowly TFA (4.63 mL). The reaction mixture was stirred at RT for 20 h, 5 eq more of TFA (4.63 mL) was added and the stirring was continued for 2 h. The reaction was concentrated in vacuo to yield the title compound as a bis-trifluoroacetate salt which was used for the next step without further purification.
LC-MS: $t_R$=0.45 min; [M+H]$^+$=265.

A.3.4 Synthesis of (R)-benzofuran-4-carboxylic acid piperidin-3-ylamide

To a cold (~0° C.) solution of (R)-3-[(benzofuran-4-carbonyl)-amino]-piperidine-1-carboxylic acid tent-butyl ester (1.4 g) in dry DCM (15 mL) was added slowly TFA (1.61 mL). The reaction mixture was stirred at RT for 20 h. The reaction was concentrated in vacuo, the resulting residue was diluted with DCM, washed with sat.NaHCO$_3$ solution. The aqueous phase was extracted twice with DCM. The combined organic extracts were washed with brine, dried (MgSO$_4$), filtered and concentrated to yield a crude light brown oil which was used for the next step without further purification.

LC-MS: $t_R$=0.62 min; [M+H]$^+$=246.

(RS)-benzofuran-4-carboxylic acid piperidin-3-ylamide is synthesized in analogy from (RS)-3-[(benzo furan-4-carbonyl)-amino]-piperidine-1-carboxylic acid tert-butyl ester.

B. Preparation of Compounds of General Formula (I): (General Procedure)

To a mixture of the respective carboxylic acid B-A-CO$_2$H (0.1 mmol, 1 eq) DIEA (0.5 mmol, 5 eq) PyBOP (0.1 mmol, 1 eq) in dry DMF (0.1 mL) was added a solution of the respective piperidine derivative (0.1 mmol, 1.0 eq, trifluoroacetate salt) in dry DMF (0.1 mL). The mixture was stirred at RT for 16 h, diluted with EA, washed with water. The aqueous phase was extracted once again with EA, the combined organic extracts were washed with brine, dried (MgSO$_4$), filtered and concentrated to yield a crude oil. The products were purified by FC (EA/n-heptane: 1/1 to EA).

EXAMPLE 1

(R)-Biphenyl-2-yl-[3-(5-bromo-pyrimidin-2-ylamino)-piperidin-1-yl]-methanone prepared by reaction of biphenyl-2-carboxylic acid with (R)-(5-bromo-pyrimidin-2-yl)-piperidine-3-yl-amine.
LC-MS: $t_R$=1.01 min; [M+H]$^+$=438.

EXAMPLE 2

(R)-[3-(5-Bromo-pyrimidin-2-ylamino)-piperidin-1-yl]-(4'-methoxy-biphenyl-2-yl)-methanone prepared by reaction of 4'-methoxy-biphenyl-2-carboxylic acid with (R)-(5-bromo-pyrimidin-2-yl)-piperidine-3-yl-amine.
LC-MS: $t_R$=1.00 min; [M+H]$^+$=468.

EXAMPLE 3

(R)-[3-(5-Bromo-pyrimidin-2-ylamino)-piperidin-1-yl]-(2'-fluoro-biphenyl-2-yl)-methanone prepared by reaction of 2'-fluoro-biphenyl-2-carboxylic acid with (R)-(5-bromo-pyrimidin-2-yl)-piperidine-3-yl-amine.
LC-MS: $t_R$=1.00 min; [M+H]$^+$=456.

EXAMPLE 4

(R)-[3-(5-Bromo-pyrimidin-2-ylamino)-piperidin-1-yl]-(3'-fluoro-biphenyl-2-yl)-methanone prepared by reaction of 3'-fluoro-biphenyl-2-carboxylic acid with (R)-(5-bromo-pyrimidin-2-yl)-piperidine-3-yl-amine.
LC-MS: $t_R$=0.95 min; [M+H]$^+$=456.

EXAMPLE 5

(R)-[3-(5-Bromo-pyrimidin-2-ylamino)-piperidin-1-yl]-(3',4'-dimethyl-biphenyl-2-yl)-methanone prepared by reaction of 3',4'-dimethyl-biphenyl-2-carboxylic acid with (R)-(5-bromo-pyrimidin-2-yl)-piperidine-3-yl-amine.
LC-MS: $t_R$=1.05 min; [M+H]$^+$=466.

EXAMPLE 6

(RS)-Benzofuran-4-carboxylic acid{1-[5-(4-fluoro-phenyl)-2-methyl-thiazole-4-carbonyl]-piperidin-3-yl}amide prepared by reaction of 5-(4-fluoro-phenyl)-2-methyl-thiazole-4-carboxylic acid with (RS)-benzofuran-4-carboxylic acid piperidin-3-ylamide.
LC-MS: $t_R$=0.96 min; [M+H]$^+$=464.

EXAMPLE 7

(R)-6-Methyl-imidazo[2,1-b]thiazole-5-carboxylic acid[1-(2-methyl-5-m-tolyl-thiazole-4-carbonyl)-piperidin-3-yl]-amide prepared by reaction of 2-methyl-5-m-tolyl-thiazole-4-carboxylic acid with (R)-6-methyl-imidazo[2,1-b]-thiazole-5-carboxylic acid-piperidin-3-ylamide.
LC-MS: $t_R$=0.82 min; [M+H]$^+$=480.

EXAMPLE 8

(R)-6-Methyl-imidazo[2,1-b]thiazole-5-carboxylic acid{1-[5-(4-fluoro-phenyl)-2-methyl-thiazole-4-carbonyl]-piperidin-3-yl}-amide prepared by reaction of 5-(4-fluoro-phenyl)-2-methyl-thiazole-4-carboxylic acid with (R)-6-methyl-imidazo[2,1-b]-thiazole-5-carboxylic acid-piperidin-3-ylamide.
LC-MS: $t_R$=0.81 min; [M+H]$^+$=484.

EXAMPLE 9

(R)-6-Methyl-imidazo[2,1-b]thiazole-5-carboxylic acid[1-(2-methyl-5-p-tolyl-thiazole-4-carbonyl)-piperidin-3-yl]-amide prepared by reaction of 2-methyl-5-p-tolyl-thiazole-4-carboxylic acid with (R)-6-methyl-imidazo[2,1-b]-thiazole-5-carboxylic acid-piperidin-3-ylamide.
LC-MS: $t_R$=0.83 min; [M+H]$^+$=480.

EXAMPLE 10

(R)-6-Methyl-imidazo[2,1-b]thiazole-5-carboxylic acid{1-[5-(4-ethyl-phenyl)-2-methyl-thiazole-4-carbonyl]-piperidin-3-yl}-amide prepared by reaction of 5-(4-ethyl-phenyl)-2-methyl-thiazole-4-carboxylic acid with (R)-6-methyl-imidazo[2,1-b]-thiazole-5-carboxylic acid-piperidin-3-ylamide.
LC-MS: $t_R$=0.87 min; [M+H]$^+$=494.

EXAMPLE 11

(R)-6-Methyl-imidazo[2,1-b]thiazole-5-carboxylic acid{1-[5-(3-fluoro-phenyl)-2-methyl-thiazole-4-carbonyl]-piperidin-3-yl}-amide prepared by reaction of 5-(3-fluoro-phenyl)-2-methyl-thiazole-4-carboxylic acid with (R)-6-methyl-imidazo[2,1-b]-thiazole-5-carboxylic acid-piperidin-3-ylamide.
LC-MS: $t_R$=0.81 min; $[M+H]^+$=484.

EXAMPLE 12

(R)-6-Methyl-imidazo[2,1-b]thiazole-5-carboxylic acid{1-[2-methyl-5-(3-trifluoro-phenyl)-thiazole-4-carbonyl]-piperidin-3-yl}-amide prepared by reaction of 2-methyl-5-(trifluoro-phenyl)-thiazole-4-carboxylic acid with (R)-6-methyl-imidazo[2,1-b]-thiazole-5-carboxylic acid-piperidin-3-ylamide.
LC-MS: $t_R$=0.88 min; $[M+H]^+$=534.

EXAMPLE 13

(R)-6-Methyl-imidazo[2,1-b]thiazole-5-carboxylic acid{1-[5-(3-chloro-phenyl)-2-methyl-thiazole-4-carbonyl]-piperidin-3-yl}-amide prepared by reaction of 5-(3-chloro-phenyl)-2-methyl-thiazole-4-carboxylic acid with (R)-6-methyl-imidazo[2,1-b]-thiazole-5-carboxylic acid-piperidin-3-ylamide.
LC-MS: $t_R$=0.84 min; $[M+H]^+$=500.

EXAMPLE 14

(R)-6-Methyl-imidazo[2,1-b]thiazole-5-carboxylic acid{1-[5-(3-methoxy-phenyl)-2-methyl-thiazole-4-carbonyl]-piperidin-3-yl}-amide prepared by reaction of 5-(3-methoxy-phenyl)-2-methyl-thiazole-4-carboxylic acid with (R)-6-methyl-imidazo[2,1-b]-thiazole-5-carboxylic acid-piperidin-3-ylamide.
LC-MS: $t_R$=0.80 min; $[M+H]^+$=496.

EXAMPLE 15

(R)-6-Methyl-imidazo[2,1-b]thiazole-5-carboxylic acid{1-[5-(2-fluoro-phenyl)-2-methyl-thiazole-4-carbonyl]-piperidin-3-yl}-amide prepared by reaction of 5-(2-fluoro-phenyl)-2-methyl-thiazole-4-carboxylic acid with (R)-6-methyl-imidazo[2,1-b]-thiazole-5-carboxylic acid-piperidin-3-ylamide.
LC-MS: $t_R$=0.80 min; $[M+H]^+$=484.

EXAMPLE 16

(R)-6-Methyl-imidazo[2,1-b]thiazole-5-carboxylic acid{1-[5-(2-chloro-phenyl)-2-methyl-thiazole-4-carbonyl]-piperidin-3-yl}-amide prepared by reaction of 5-(2-chloro-phenyl)-2-methyl-thiazole-4-carboxylic acid with (R)-6-methyl-imidazo[2,1-b]-thiazole-5-carboxylic acid-piperidin-3-ylamide.
LC-MS: $t_R$=0.83 min; $[M+H]^+$=500.

EXAMPLE 17

(R)-6-Methyl-imidazo[2,1-b]thiazole-5-carboxylic acid{1-[5-(3,4-dimethyl-phenyl)-2-methyl-thiazole-4-carbonyl]-piperidin-3-yl}-amide prepared by reaction of 5-(3,4-dimethyl-phenyl)-2-methyl-thiazole-4-carboxylic acid with (R)-6-methyl-imidazo[2,1-b]-thiazole-5-carboxylic acid-piperidin-3-ylamide.
LC-MS: $t_R$=0.86 min; $[M+H]^+$=494.

EXAMPLE 18

(R)-6-Methyl-imidazo[2,1-b]thiazole-5-carboxylic acid{1-[5-(4-chloro-phenyl)-2-methyl-thiazole-4-carbonyl]-piperidin-3-yl}-amide prepared by reaction of 5-(4-chloro-phenyl)-2-methyl-thiazole-4-carboxylic acid with (R)-6-methyl-imidazo[2,1-b]-thiazole-5-carboxylic acid-piperidin-3-ylamide.
LC-MS: $t_R$=0.82 min; $[M+H]^+$=500.

EXAMPLE 19

(R)-6-Methyl-imidazo[2,1-b]thiazole-5-carboxylic acid{1-[5-(3,4-difluoro-phenyl)-2-methyl-thiazole-4-carbonyl]-piperidin-3-yl}-amide prepared by reaction of 5-(3,4-difluoro-phenyl)-2-methyl-thiazole-4-carboxylic acid with (R)-6-methyl-imidazo[2,1-b]-thiazole-5-carboxylic acid-piperidin-3-ylamide.
LC-MS: $t_R$=0.83 min; $[M+H]^+$=502.

EXAMPLE 20

[(R)-3-(5-Bromo-pyrimidin-2-ylamino)-piperidin-1-yl]-[5-(3,4-dimethyl-phenyl)-2 methyl-thiazol-4-yl]-methanone prepared by reaction of (R)-(5-bromo-pyrimidin-2-yl)-piperidin-3-yl-amine with 5-(3,4-dimethyl-phenyl)-2-methyl-thiazole-4-carboxylic acid.
LC-MS: $t_R$=1.00 min; $[M+H]^+$=486.46.

EXAMPLE 21

Benzofuran-4-carboxylic acid [(R)-1-(biphenyl-2-carbonyl)-piperidin-3-yl]amide prepared by reaction of (R)-benzofuran-4-carboxylic acid piperidin-3-ylamide with biphenyl-2-carboxylic acid acid.
LC-MS: $t_R$=0.99 min; $[M+H]^+$=425.17.

EXAMPLE 22

6-Methyl-imidazo[2,1-b]thiazole-5-carboxylic acid [(R)-1-(3'-chloro-biphenyl-2-carbonyl)-piperidin-3-yl]-amide prepared by reaction of (R)-6-methyl-imidazo[2,1-b]thiazole-5-carboxylic acid piperidin-3-ylamide with 3'-chloro-biphenyl-2-carboxylic acid.
LC-MS: $t_R$=0.87 min; $[M+H]^+$=479.48.

EXAMPLE 23

6-Methyl-imidazo[2,1-b]thiazole-5-carboxylic acid [(R)-1-(3'-methyl-biphenyl-2-carbonyl)-piperidin-3-yl]-amide prepared by reaction of (R)-6-methyl-imidazo[2,1-b]thiazole-5-carboxylic acid piperidin-3-ylamide with 3'-methyl-biphenyl-2-carboxylic acid.

LC-MS: $t_R$=0.87 min; $[M+H]^+$=479.48.

II. Biological Assays

In Vitro Assay

The orexin receptor antagonistic activity of the compounds of formula (I) is determined in accordance with the following experimental method.

Experimental Method:

Intracellular Calcium Measurements:

Chinese hamster ovary (CHO) cells expressing the human orexin-1 receptor and the human orexin-2 receptor, respectively, are grown in culture medium (Ham F-12 with L-Glutamine) containing 300 µg/ml G418, 100 U/ml penicillin, 100 µg/ml streptomycin and 10% inactivated fetal calf serum (FCS). The cells are seeded at 80'000 cells/well into 96-well black clear bottom sterile plates (Costar) which have been precoated with 1% gelatine in Hanks' Balanced Salt Solution (HBSS). All reagents are from Gibco BRL. The seeded plates are incubated overnight at 37° C. in 5% $CO_2$.

Human orexin-A as an agonist is prepared as 1 mM stock solution in methanol:water (1:1), diluted in HBSS containing 0.1% bovine serum albumin (BSA) and 2 mM HEPES for use in the assay at a final concentration of 10 nM.

Antagonists are prepared as 10 mM stock solution in DMSO, then diluted in 96-well plates, first in DMSO, then in HBSS containing 0.1% bovine serum albumin (BSA) and 2 mM HEPES.

On the day of the assay, 100 µl of loading medium (HBSS containing 1% FCS, 2 mM HEPES, 5 mM probenecid (Sigma) and 3 µM of the fluorescent calcium indicator fluo-3 AM (1 mM stock solution in DMSO with 10% pluronic acid) (Molecular Probes) is added to each well.

The 96-well plates are incubated for 60 min at 37° C. in 5% $CO_2$. The loading solution is then aspirated and cells are washed 3 times with 200 µl HBSS containing 2.5 mM probenecid, 0.1% BSA, 2 mM HEPES. 100 µl of that same buffer is left in each well.

Within the Fluorescent Imaging Plate Reader (FLIPR, Molecular Devices), antagonists are added to the plate in a volume of 50 µl, incubated for 20 min and finally 100 µl of agonist is added. Fluorescence is measured for each well at 1 second intervals, and the height of each fluorescence peak is compared to the height of the fluorescence peak induced by 10 nM orexin-A with buffer in place of antagonist. For each antagonist, $IC_{50}$ value (the concentration of compound needed to inhibit 50% of the agonistic response) is determined.

Antagonistic activities ($IC_{50}$ values) of all exemplified compounds are below 1000 nM with respect to the $OX_1$ and/or the $OX_2$ receptor. $IC_{50}$ values of 23 exemplified compounds are in the range of 8-1784 nM with an average of 357 nM with respect to the $OX_1$ receptor. $IC_{50}$ values of all exemplified compounds are in the range of 49-1159 nM with an average of 292 nM with respect to the $OX_2$ receptor. Antagonistic activities of selected compounds are displayed in Table 1.

TABLE 1

| Compound of Example | $OX_1$ $IC_{50}$ (nM) | $OX_2$ $IC_{50}$ (nM) |
|---|---|---|
| 1 | 294 | 392 |
| 3 | 81 | 171 |
| 7 | 27 | 50 |
| 9 | 101 | 165 |
| 15 | 65 | 97 |

The invention claimed is:

1. A compound of formula (I)

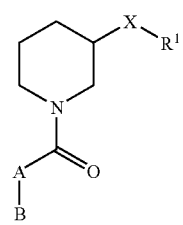

wherein

X—$R^1$ represents —N(H)-pyrimidinyl, wherein said pyrimidinyl is unsubstituted or mono-substituted wherein the substituent is selected from $(C_{1-4})$alkyl or halogen, or X—$R^1$ represents —NH—C(O)-heterocyclyl, wherein the heterocyclyl is selected from benzofuranyl and imidazo[2,1-b]-thiazolyl, wherein said heterocyclyl is unsubstituted or independently mono-, di-, or tri-substituted wherein the substituents are independently selected from $(C_{1-4})$alkyl;

A represents a phenyl- or thiazolyl-group, wherein the phenyl or thiazolyl is unsubstituted or mono-substituted with $(C_{1-4})$alkyl;

B represents a phenyl-group, wherein the phenyl is unsubstituted or mono-, or di-substituted, wherein the substituents are independently selected from the group consisting of $(C_{1-4})$alkyl, $(C_{1-4})$alkoxy, trifluoromethyl, cyano and halogen;

or a salt of such compound.

2. A compound according to claim 1, wherein the stereogenic center in position 3 of the piperidine ring is in absolute (R)-configuration

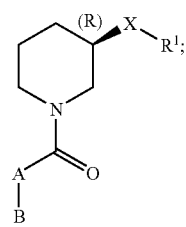

or a salt of such compound.

3. The compound according to claim 1, wherein

A represents a phenyl- or thiazolyl-group, wherein the phenyl or thiazolyl is unsubstituted or mono-substituted with $(C_{1-4})$alkyl; and B represents a phenyl-group, wherein the phenyl is mono-, or di-substituted, wherein the substituents are independently selected from the group consisting of $(C_{1-4})$alkyl, $(C_{1-4})$alkoxy, trifluoromethyl, and halogen;
or a salt of such compound.

4. The compound according to claim 1, wherein
A represents a thiazolyl-group, wherein the thiazolyl is unsubstituted or mono-substituted with $(C_{1-4})$alkyl;
B represents a phenyl-group, wherein the phenyl is mono-, or di-substituted, wherein the substituents are independently selected from the group consisting of methyl, ethyl, methoxy, trifluoromethyl, fluorine and chlorine;
or a salt of such compound.

5. The compound according to claim 1, wherein
$X—R^1$ represents —N(H)pyrimidinyl, wherein said pyrimidinyl is mono-substituted wherein the substituent is selected from $(C_{1-4})$alkyl or halogen, or
$X—R^1$ represents —NH—C(O)imidazo[2,1-b]-thiazolyl, wherein said imidazo[2,1-b]-thiazolyl is mono-, di-, or tri-substituted wherein the substituents are independently selected from $(C_{1-4})$alkyl;
or a salt of such compound.

6. The compound according to claim 1, wherein $X—R^1$ represents —NH—C(O)imidazor[2,1-b]-thiazolyl, wherein said imidazo[2,1-b]-thiazolyl is unsubstituted or mono-, di-, or tri-substituted wherein the substituents are independently selected from $(C_{1-4})$alkyl; or a salt of such compound.

7. The compound according to claim 1, wherein
$X—R^1$ represents —NH—C(O)-heterocyclyl, wherein the heterocyclyl is selected from benzofuranyl and imidazo[2,1-b]-thiazolyl, wherein said heterocyclyl is unsubstituted or independently mono-, di-, or tri-substituted wherein the substituents are independently selected from $(C_{1-4})$alkyl;
or a salt of such compound.

8. The compound according to claim 1 selected from the group consisting of:
(R)-Biphenyl-2-yl-[3-(5-bromo-pyrimidin-2-ylamino)-piperidin-1-yl]-methanone;
(R)-[3-(5-Bromo-pyrimidin-2-ylamino)-piperidin-1-yl]-(4'-methoxy-biphenyl-2-yl)-methanone;
(R)-[3-(5-Bromo-pyrimidin-2-ylamino)-piperidin-1-yl]-(2'-fluoro-biphenyl-2-yl)-methanone;
(R)-[3-(5-Bromo-pyrimidin-2-ylamino)-piperidin-1-yl]-(3'-fluoro-biphenyl-2-yl)-methanone;
(R)-[3-(5-Bromo-pyrimidin-2-ylamino)-piperidin-1-yl]-(3',4'-dimethyl-biphenyl-2-yl)-methanone;
(R)-Benzofuran-4-carboxylic acid {1-[5-(4-fluoro-phenyl)-2-methyl-thiazole-4-carbonyl]-piperidin-3-yl}amide;
(R)-6-Methyl-imidazo[2,1-b]thiazole-5-carboxylic acid [1-(2-methyl-5-m-tolyl-thiazole-4-carbonyl)-piperidin-3-yl]-amide;
(R)-6-Methyl-imidazo[2,1-b]thiazole-5-carboxylic acid{1-[5-(4-fluoro-phenyl)-2-methyl-thiazole-4-carbonyl]-piperidin-3-yl}-amide;
(R)-6-Methyl-imidazo[2,1-b]thiazole-5-carboxylic acid [1-(2-methyl-5-p-tolyl-thiazole-4-carbonyl)-piperidin-3-yl]amide;
(R)-6-Methyl-imidazo[2,1-b]thiazole-5-carboxylic acid{1-[5-(4-ethyl-phenyl)-2-methyl-thiazole-4-carbonyl]piperidin-3-yl}-amide;
(R)-6-Methyl-imidazo[2,1-b]thiazole-5 -carboxylic acid{1-[5-(3-fluoro-phenyl)-2-methyl-thiazole-4-carbonyl]-piperidin-3-yl}-amide;
(R)-6-Methyl-imidazo[2,1-b]thiazole-5-carboxylic acid{1-[2methyl-5-(3-trifluoro-phenyl)-thiazole-4-carbonyl]-piperidin-3-yl}-amide;
(R)-6-Methyl-imidazo[2,1-b]thiazole-5-carboxylic acid{1-[5-(3-chloro-phenyl)-2-methyl-thiazole-4-carbonyl]-piperidin-3-yl}-amide;
(R)-6-Methyl-imidazo[2,1-b]thiazole-5-carboxylic acid{1-[5-(3-methoxy-phenyl)-2-methyl-thiazole-4-carbonyl]-piperidin-3-yl}-amide;
(R)-6-Methyl-imidazo[2,1-b]thiazole-5-carboxylic acid{1-[5-(2-fluoro-phenyl)-2-methyl-thiazole-4-carbonyl]-piperidin-3-yl}-amide;
(R)-6-Methyl-imidazo[2,1-b]thiazole-5-carboxylic acid{1-[5-(2-chloro-phenyl)-2-methyl-thiazole-4-carbonyl]-piperidin-3-yl}-amide;
(R)-6-Methyl-imidazo[2,1-b]thiazole-5-carboxylic acid{1-[5-(3,4-dimethyl-phenyl)-2-methyl-thiazole-4-carbonyl]-piperidin-3-yl}-amide;
(R)-6-Methyl-imidazo[2,1-b]thiazole-5-carboxylic acid{1-[4-chloro-phenyl)-2-methyl-thiazole-4-carbonyl]-piperidin-3-yl}-amide; and
(R)-6-Methyl-imidazo[2,1-b]thiazole-5-carboxylic acid{1-[5-(3,4-difluoro-phenyl)-2-methyl-thiazole-4-carbonyl]-piperidin-3-yl}-amide;
[(R)-3-(5-Bromo-pyrimidin-2-ylamino)-piperidin-1-yl]-[5-(3,4-dimethyl-phenyl)-2methyl-thiazole-4-yl]-methanone;
Benzofuran-4-carboxylic acid [(R)-1-(biphenyl-2-carbonyl)-piperidin-3-yl]amide;
6-Methyl-imidazo[2,1-b]thiazole-5-carboxylic acid [(R)-1-(3'-chloro-biphenyl-2-carbonyl)-piperidin-3-yl]-amide; and
6-Methyl-imidazo[2,1-b]thiazole-5-carboxylic acid [(R)-1-(3'-methyl-biphenyl-2-carbonyl)-piperidin-3-yl]-amide;
or a salt of such compound.

9. A pharmaceutical composition comprising the compound according to claim 1 in free or pharmaceutically acceptable salt form and an inert carrier material.

10. A method for the treatment of insomnias or anxiety disorders comprising administering to a subject in need thereof a pharmaceutically active amount of a compound according to claim 1, in free or pharmaceutically acceptable salt form.

* * * * *